(12) United States Patent
Kobrehel et al.

(10) Patent No.: US 6,369,035 B1
(45) Date of Patent: Apr. 9, 2002

(54) 3,6-HEMIKETALS FROM THE CLASS OF 9A-AZALIDES

(75) Inventors: Gabrijela Kobrehel; Gorjana Lazarevski, both of Zagreb; Mladen Vinkovic, Čakovec, all of (HR)

(73) Assignee: Pliva, farmaceutska industrja, dioničko društvo, Zagreb (HR)

( * ) Notice: Subject to any disclaimer, the term of this patent is extended or adjusted under 35 U.S.C. 154(b) by 0 days.

(21) Appl. No.: 09/529,642

(22) PCT Filed: Oct. 13, 1998

(86) PCT No.: PCT/HR98/00005

§ 371 Date: Apr. 17, 2000

§ 102(e) Date: Apr. 17, 2000

(87) PCT Pub. No.: WO99/20639

PCT Pub. Date: Apr. 29, 1989

(30) Foreign Application Priority Data

Oct. 16, 1997 (HR) ................................................ 970551
Sep. 10, 1998 (HR) ................................................ 980497

(51) Int. Cl.$^7$ ........................... A61K 31/70; C07H 17/08
(52) U.S. Cl. .......................................... 514/29; 536/7.4
(58) Field of Search .............................. 536/7.4; 514/29

(56) References Cited

U.S. PATENT DOCUMENTS 4,963,531 A * 10/1990 Remington ................... 514/29
5,250,518 A * 10/1993 Kobrel et al. ................. 514/29

* cited by examiner

*Primary Examiner*—Elli Peselev
(74) *Attorney, Agent, or Firm*—Connolly Bove Lodge & Hut

(57) ABSTRACT

The invention relates to novel compounds from the class of macrolide antibiotics. Particularly, the invention relates to novel 3,6-heiketals from the class of 9a-azalides, to their pharmaceutically acceptable addition salts with inorganic or organic acids, to a process for their preparation and to the use thereof as antibiotics or as intermediates for the synthesis of other macrolide antibiotics.

21 Claims, No Drawings

3,6-HEMIKETALS FROM THE CLASS OF 9A-AZALIDES

TECHNICAL FIELD OF THE INVENTION

A61 K 31/70, C 07 H 17/08

TECHNICAL PROBLEM

The invention relates to novel compounds from the class of macrolide antibiotics. Particularly, the invention relates to novel 3,6-hemiketals from the class of 9a-azalides, to their pharmaceutically acceptable addition salts with inorganic or organic acids, to a process for their preparation and to the use thereof as antibiotics or as intermediates for the synthesis of other macrolide antibiotics.

PRIOR ART

Macrolide antibiotic erythromycin A has been for more than 40 years considered as a safe and efficient agent for the treatment of respiratory and genital infections caused by Gram-positive and by some Gram-negative bacteria, some species of Legionella, Mycoplasma, Chlamidia and Helicobacter. Noticed changes in bioavailability after oral administration, gastric intolerance in many patients and loss of activity in an acidic medium whereat the inactive metabolite anbydroerythromycin is formed are basic disadvantages in the clinical use of eiythromycin. However, the spirocyclization of the aglycone ring is successfully inhibited by a chemical transformation of C-9 ketone or hydroxyl groups in C-6 and/or C-12 positions. Thus, e.g by oximation of C-9 ketone and subsequent Beckmann rearrangement and reduction, 9-deoxo-9a-aza-9a-homoerythromycin A, the first 15-membered macrolide antibiotic with 9a-amino group incorporated in the aglycone ring, is obtained (Kobrehel G. et al., U.S. Pat. No. 4,328,334; May 1982). By reductive methylation of 9-amines according to Eschweiler-Clark process, 9-deoxo-9a-methyl-9a-aza-9a-homoerythromycin (AZITHROMYCIN), a prototype of a novel class of macrolide antibiotics, namely azalides, is synthesized (Kobrehel G. et al., BE 892357; July 1982). In addition to a broad antimicrobial spectrum including also Gram-negative bacteria, azithromycin is also characterized by a long biological half-life, a specific transport mechanism to the place of use and a short therapy period. Azithromycin easily penetrates and it accumulates inside human phagocyte cells resulting in an improved action upon intracellular pathogenic micro-organisms from the classes of Legionella, Chlamidia and Helicobacter.

Further, it is known that C-6/C-12 spirocyclization of erythromycin A is successfully inhibited by O-methylation of C-6 hydroxyl group of the aglycone ring (Watanabe Y. et al., U.S. Pat. No. 4,331,803; May 1982). By the reaction of erythromycin with benzyloxycarbonyl chloride and subsequent methylation of the obtained 2'-O,3'-N-bis(benzyloxycarbonyl) derivative, by elimination of the protecting groups and by 3'-N-methylation, there are formed, in addition to 6-O-methylerythromycin (CLARITHROMYCIN), also significant amounts of 11-O-methylerythromycin and of multiple-substituted analogs (Morimoto S., et al., J. Antibiotics, 1984, 37, 187). With respect to erytlromycin A, clarithromycin is considerably more stable in an acidic medium and exhibits better in vitro action with respect to Gram-positive bacteria strains (Kirst H. A. et al., Antimicrobial Agents and Chemoter., 1989, 1419). In a similar manner also a series of O-methyl-derivatives of azithromycin (Kobrehel G. et al., U.S. Pat. No. 5,250,518; October 1993) was synthesized. Although the main products of O-methylation of azithromycin, namely 11-O-methyl-azithromycin (Example 8) and 6-O-methyl-azithromycin (Example 6) exhibit significant activity against standard bacteria strains and clinical isolates and pharmacokinetic properties similar to those of azithromycin, the obtaining of products in larger quantities represents an additional technical problem due to nonselectivity of O-methylation. The determination of the structure of O-methyl-derivatives of azithromycin was based on analysis of $^1$H-$^1$H and $^1$H-$^{13}$C 2D NMR spectra (300 MHz). Subsequently, it was additionally determined by long-range NMR spectroscopy that substitution on C-6 hydroxyl group had been erroneously ascribed to azithromycin and that actually 12-O-methyl-azithromycin was in question. Further it has been found that the use of suitable protecting groups on hydroxyl groups in 4"- and 11-positions (especially of silyl protecting groups such as trimethylsilyl groups) results in selective O-methylation and makes possible a simple preparation of 12-O-methyl-azithromycin (HR 970051A; October 1997). Later, Waddell S. T. et al., (Biorg. Med. Chem. Letters 8 (1998), 549–555), independently of the latter patent application, established O-methylation of hydroxyl group in C-12 position.

It is known as well that recent research on 14-membered macrolides has lead to the discovery of a new type of macrolide antibiotics, namely ketolides. Instead of the neutral sugar L-cladinose known for its unstability even in a weakly acidic medium, these compounds possess a keto group on C-3 position (Agouridas C. et al., EP 596802 A1, May 1994; Le Martret O., FR 2697524 A1, May 1994). Ketolides show a significantly better action against MLS (macrolide, lincosamide and streptogramin B) induced-resistant organisms (Jamjian C., Antimicrob. Agents Chemother., 1997, 41, 485). This important discovery has led to a large number of 3-keto derivatives of clarithromycin, mostly substituted on C-11/C-12 positions, yielding numerous cyclic carbonates, carbamates and, recently, carbazates. The first step of the synthesis of ketolides includes the hydrolysis of clarithromycin under the formation of a corresponding 3-decladinosyl derivative, (3-de(2,6-dideoxy-3-C-methyl-3-O-methyl-α-L-ribohexopyranosyl-oxy)-derivative), which is, after the removal of the protection of 2'-hydroxyl group (preferably by acylation with chlorides or anhydrides of carboxylic acids), subjected to a reaction of oxidation and deprotection of 2'- position. According to our knowledge C-11/C-12 substituted ketolides from the class of 9a-azalide antibiotics have hitherto not been described. The first step, namely the synthesis of 3-decladinosyl-derivatives of 9-deoxo-9a-aza-9a-homoerydiromycin and azithromycin, is described in U.S. Pat. No. 4,886,792, December 1989. With intention to oxidize C-3 hydroxyl group of 3-decladinosyl-azithromycin and its 11-O-methyl- and 12-O-methyl-derivatives by transannular addition of 6-hydroxyl group onto the newly formed C-3 ketone there has been obtained a hitherto not described series of bicyclic and tricyclic 3,6-hemiketals from the class of 9a-azalides.

The synthesis of 3,6-hemiketals of azithromycin and O-methyl derivatives thereof comprises the preparation of corresponding 3-decladinosyl derivatives, the protection of 2'-hydroxyl group of the basic sugar, D-desosamine, by selective acylation, the oxidation of the hydroxyl group in C-3 position, the deprotection of 2'-position and the cyclization of C-11 and C-12 hydroxyl groups. Objects of the present invention are also pharmaceutically acceptable addition salts of 3,6-hemiketals of azithromycin and its O-methyl derivatives with organic and inorganic acids, methods and intermediates for their preparation, as well as preparation and application methods of pharmaceutical preparations.

DESCRIPTION OF TECHNICAL PROBLEM WITH EXAMPLES

The invention relates to i) novel 3,6-hemiketals from the class of 9a-azalides, ii) a process for the preparation of novel 3,6-hemiketals from the class of 9a-azalides.

iii) use of novel 3,6-hemiketals from the class of 9a-azalides as antibiotics or as intermediates for the synthesis of other macrolide antibiotics.

Novel 3,6-hemiketals from the class of 9a-azalides of the general formula (I)

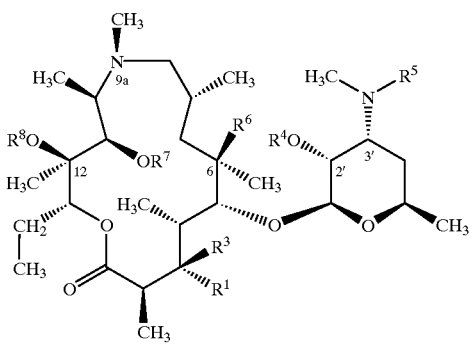

(I)

characterized in that

R$^1$ individually stands for hydroxyl, L-cladinosyl group of the formula (II)

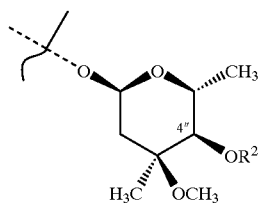

(II)

wherein

R$^2$ individually stands for hydrogen or a silyl group,

R$^3$ individually stands for hydrogen or together with R$^6$ stands for an ether group, R$^4$ individually stands for hydrogen, (C$_1$–C$_4$)acyl group or —COO—(CH$_2$)$_n$—Ar group, wherein n is 1–7 and Ar individually stands for an unsubstituted or substituted aryl group with up to 18 carbon atoms, R$^5$ individually stands for hydrogen, methyl group or —COO—(CH$_2$)$_n$—Ar group, wherein n is 1–7 and Ar individually stands for an unsubstituted or substituted aryl group with up to 18 carbon atoms, R$^6$ individually stands for a hydroxyl group or together with R$^3$ has the meaning of an ether group, R$^7$ individually stands for hydrogen, (C$_1$–C$_{12}$)alkyl group, silyl group or together with R$^8$ and C-11/C-12 carbon atoms stands for a cyclic carbonate, R$^8$ individually stands for hydrogen, (C$_1$–C$_{12}$)alkyl group, silyl group or together with R$^7$ and C-11/C-12 carbon atoms stands for a cyclic carbonate, and their pharmaceutically acceptable addition salts with inorganic or organic acids, are obtained by the following steps.

Step 1

Azithromycin of the general formula (I) wherein R$^1$ stands for L-cladinosyl group of the formula (II), R$^2$, R$^3$, R$^4$, R$^7$ and R$^8$ are mutually the same and stand for hydrogen, R$^5$ is methyl and R$^6$ is a hydroxyl group, is subjected to a reaction with organic carboxylic acid chlorides of the formula (III)

ClCOO(CH$_2$)$_n$—Ar     (III)

wherein n is 1–7 and Ar individually stands for unsubstituted or substituted aryl groups with up to 18 carbon atoms, preferably with benzyloxycarbonyl chloride, in the presence of bases, preferably sodium hydrogen carbonate, in a reaction-inert solvent, preferably in benzene or toluene, yielding 2'-O,3'-N-bis(bezyloxycarbonyl)-3'(Kobrehel G. et al., U.S. Pat. No. 5,250,518; May 1993) of the general formula (I), wherein R$^1$ stands for L-cladinosyl group of the formula (II), R$^2$, R$^3$, R$^7$ and R$^8$ are mutually the same and stand for hydrogen, R$^4$ and R$^5$ are mutually the same and stand for benzyloxycarbonyl group and R$^6$ is hydroxyl group, which is subsequently subjected to silylation of hydroxyl groups in A/ 4"- and 11-positions with 2–5 equimolar excess of a silylating agent, in an organic inert solvent, at the temperature of 0–5° C. during 5–8 hours, yielding novel 4"-11-O-bis(trimethylsilyl)-2'-O,3'-N-bis(benzyloxycarbonyl)-3'-N-demethyl-azithromycin of the general formula (I), wherein R$^1$ stands for L-cladinosyl group of the formula (II), R$^2$ and R$^7$ are mutually the same and stand for trimethylsilyl group, R$^3$ and R$^8$ are mutually the same and stand for hydrogen, R$^4$ and R$^5$ are mutually the same and stand for benzyloxycarbonyl group and R$^6$ is hydroxyl group, or in B/ 4"-position with 1.1–2 equimolar excess of a silylating agent, in an organic inert solvent, at the temperature of 0–5° C. during 1 hour, yielding novel 4"-O-trimethylsilyl-2'-O,3'-N-bis(benzyloxycarbonyl)-3'-N-demethyl-azithromycin of the general formula (I), wherein R$^1$ stands for L-cladinosyl group of the formula (II), R$^2$ stands for trimethylsilyl group, R$^3$, R$^7$ and R$^8$ are mutually the same and stand for hydrogen, R$^4$ and R$^5$ are mutually the same and stand for benzyloxycarbonyl group and R$^6$ stands for hydroxyl group.

As silylating agents there are used 1,1,1,3,3,3-hexamethyldisilazane, trimethylsilyl chloride, bis(trimethylsilyl)acetamide and similar agents for introducing trimethylsilyl group, preferably a mixture of trimethylsilyl chloride and trimethylsilyl imidazole. As a suitable solvent pyridine, ethyl acetate, N,N-dimethylformamide, methylene chloride and the like, preferably pyridine are used.

Step 2

By a reaction of 4",11-O-bis(trimethylsilyl)-2'-O,3'-N-bis(benzyloxycarbonyl)-3'-N-demethyl-azithromycin from the step 1A/or 4"-O-trimethylsilyl-2'-O,3'-N-bis(benzyloxycarbonyl)-3'-N-demethyl-azithromycin from the step 1B/, respectively, with 1.3–10 moles of a corresponding alkylating agent, preferably methylating agent, in the presence of 1.1–8.5 moles of a suitable base, at a temperature from −15° C. to room temperature, preferably at 0–5° C., in a suitable reaction-inert solvent, there comes to A/ a selective alkylation, preferably methylation of C-12 hydroxyl group yielding a novel 4"-11-O-bis (trimethylsilyl)-2'-O,3'-N-bis(benzyloxycarbonyl)-3'-N-demethyl-12-O-methyl-azithromycin of the general formula (I), wherein $R^1$ stands for L-cladinosyl group of the formula (II), $R^2$ and $R^7$ are mutually the same and stand for trimethylsilyl group, $R^3$ stands for hydrogen, $R^4$ and $R^5$ are mutually the same and stand for benzyloxycarbonyl group, $R^6$ is hydroxyl group and $R^8$ is methyl, or B/ an alkylation, preferably methylation of C-11 or C-12 hydroxyl group yielding a mixture of novel 4"-O-trimethylsilyl-2'-O,3'-N-bis(benzyloxycarbonyl)-3'-N-demethyl-11-O-methyl-azithromycin of the general formula (I), wherein $R^1$ stands for L-cladinosyl group of the formula (II), $R^2$ stands for trimethylsilyl group, $R^3$ and $R^8$ are mutually the same and stand for hydrogen, $R^4$ and $R^5$ are mutually the same and stand for benzyloxycarbonyl group, $R^6$ stands for hydroxyl group and $R^7$ is methyl, or 4"-O-trimethylsilyl-2'-O,3'-N-bis(benzyloxycarbonyl)-3'-N-demethyl-12-O-methyl-azithromycin of the general formula (I), wherein $R^1$ stands for L-cladinosyl group of the formula (II), $R^2$ stands for trimethylsilyl group, $R^3$ and $R^7$ are mutually the same and stand for hydrogen, $R^4$ and $R^5$ are mutually the same and stand for benzyloxycarbonyl group, $R^6$ stands for hydroxyl group and $R^8$ is methyl.

As suitable alkylating agents there are used ($C_1$–$C_{12}$)alkyl halides, preferably methyl iodide, dimethyl sulfate, methyl methane sulfonate or methyl p-toluene sulfonate, preferably methyl iodide. Suitable bases are alkali metal hydride (lithium hydride, sodium hydride or potassium hydride), alkali metal hydroxide (potassium hydroxide or sodium hydroxide) or alkali metal methyl amide (lithium amide, sodium amide or potassium amide), preferably sodium hydride. Suitable reaction-inert solvents are dimethyl sulfoxide, N,N-dimethyl formamide, N,N-dimethyl acetamide or hexamethyl phosphoric triamide, preferably N,N-dimethyl formamide, dimethyl sulfoxide or a mixture thereof with tetrahydrofuran.

Step 3

4"-11-O-Bis(trimethylsilyl)-2'-O,3'-N-bis(benzyloxycarbonyl)-3'-N-demethyl-12-O-methyl-azithromycin from the step 2A/ or the obtained mixture of 4"-O-trimethylsilyl-2'-O,3'-N-bis(benzyloxycarbonyl)-3'-N-demethyl-11-O-methyl-azithromycin and 4"-O-trimethylsilyl-2'-O,3'-N-bis(benzyloxycarbonyl)-3'-N-demethyl-12-O-methyl-azithromycin from the step 2B/ is subjected to a hydrogenolysis reaction according to the method by E. H. Flynn et al. (Journal of American Chemical Society, 77, 3104, 1950) in order to deprotect protecting groups on 2'- and 3'-positions and then to desilylation according to the conventional process in lower alcohols, preferably isopropanol in the presence of formic acid in A/ 4"- and 11-positions in the step 2A/ yielding 3'-N-demethyl-12-O-methyl-azithromycin of the general formula (I) wherein $R^1$ stands for L-cladinosyl group of the formula (II), $R^2$, $R^3$, $R^4$, $R^5$ and $R^7$ are mutually the same and stand for hydrogen, $R^6$ is hydroxyl group and $R^8$ is methyl, or in B/ 4"-position in the Step 2B/ yielding a mixture of 3'-N-demethyl-11-O-methyl-azithromycin of the general formula (I), wherein $R^1$ stands for L-cladinosyl group of the formula (II), $R^2$, $R^3$, $R^4$, $R^5$ and $R^8$ are mutually the same and stand for hydrogen, $R^6$ is hydroxyl group and $R^7$ is methyl, and 3'-N-demethyl-12-O-methyl-azithromycin of the general formula (I), wherein $R^1$ stands for L-cladinosyl group of the formula (II), $R^2$, $R^3$, $R^4$, $R^5$ and $R^7$ are mutually the same and stand for hydrogen, $R^6$ is hydroxyl group and $R^8$ is methyl.

Hydrogenolysis is carried out in a solution of lower alcohols, preferably in ethanol, in the presence of NaOAc/HOAc buffer (pH 5) with a catalyst such as palladium black or palladium on charcoal, at a hydrogen pressure from 1 to 20 bars, at room temperature.

Step 4

3'-N-Demethyl-12-O-methyl-azithromycin from the step 3A/ or the obtained mixture of 3'-N-demethyl-11-O-methyl-azithromycin and 3'-N-demethyl-12-O-methyl-azithromycin from the Step 3B/ is subjected to a reductive 3'-N-methylation with 1-3 equivalents of formaldehyde (37%) in the presence of an equal or double quantity of formic acid (98–100%) and hydrogenation catalyst or of some other hydrogen source, in a reaction-inert solvent such as halogenated hydrocarbons, lower alcohols or lower ketones, preferably chloroform, at the reflux temperature of the reaction mixture, yielding—in the case of the compound from the Step 3A/—12-O-methyl-azithromycin of the general formula (I), wherein $R^1$ stands for L-cladinosyl group of the formula (II), $R^2$, $R^3$, $R^4$ and $R^7$ are mutually the same and stand for hydrogen, $R^5$ and $R^8$ are mutually the same and stand for methyl and $R^6$ is hydroxyl group, or—in the case of products from the Step 3B/—a mixture of 11-methyl-azithromycin of the general formula (I), wherein $R^1$ stands for L-cladinosyl group of the formula (II), $R^2$, $R^3$, $R^4$ and $R^8$ are mutually the same and stand for hydrogen, $R^5$ and $R^7$ are mutually the same and stand for methyl and $R^6$ is hydroxyl group, and of 12-O-methyl-azithromycin of the general formula (I), wherein $R^1$, $R^2$, $R^3$, $R^4$, $R^5$, $R^6$, $R^7$ and $R^8$ have the meanings as given in the case of 3'-N-methylation of the compounds from the Step 3A/.

Step 5

Azithromycin of the general formula (I), wherein $R^1$ stands for L-cladinosyl group of the formula (II), $R^2$, $R^3$, $R^4$, $R^7$ and $R^8$ are mutually the same and stand for hydrogen, $R^5$ is methyl and $R^6$ is hydroxyl group, or its 11-O-methyl- and 12-O-methyl-derivatives from the Step 4 are optionally subjected to hydrolysis with strong acids, preferably with 0.25–1.5 N hydrochloric or dichloroacetic acid in a mixture of water and an alcohol, preferably methanol, ethanol or isopropanol, for 10–30 hours, at room temperature yielding 3-de(2,6-dideoxy-3-C-methyl-3-O-methyl-α-L-ribohexopyranosyl-oxy)-3-oxy-azithromycin of the general formula (I), wherein $R^1$ and $R^6$ are mutually the same and stand for hydroxyl group, $R^3$, $R^4$, $R^7$ and $R^8$ are mutually the same and stand for hydrogen and $R^5$ is methyl, or 3-de(2,6-dideoxy-3-C-methyl-3-O-methyl-α-L-ribohexopyranosyl-oxy)-3-oxy-11-O-methyl-azithromycin of the general formula (I), wherein $R^1$ and $R^6$ are mutually the same and stand for hydroxyl group, $R^3$, $R^4$ and $R^8$ are mutually the same and stand for hydrogen and $R^5$ and $R^7$ are mutually the same and stand for methyl, or 3-de(2,6-dideoxy-3-C-methyl-3-O-methyl-α-L-ribohexopyranosyl-oxy)-3-oxy-12-O-methyl-azithromycin of the general formula (I), wherein $R^1$ and $R^6$ are mutually the same and stand for hydroxyl group, $R^3$, $R^4$ and $R^7$ are mutually the same and stand for hydrogen and $R^5$ and $R^8$ are mutually the same and stand for methyl.

Step 6

3-De(2,6-dideoxy-3-C-methyl-3-O-methyl-α-L-ribohexopyranosyl-oxy)-3-oxy-azithromycin and its 11-O-methyl- and 12-O-methyl derivatives from the Step 5 are subjected to a selective acylation of the hydroxyl group in 2'-position. Acylation is carried out with chlorides or anhydrides of carboxylic acids with up to 4 carbon atoms, preferably with acetic acid anhydride, in the presence of inorganic or organic bases, in a reaction-inert organic solvent, at a temperature from 0–30° C., yielding 3-de(2,6-dideoxy-3-C-methyl-3-O-methyl-α-L-ribohexopyranosyl-oxy)-3-oxy-azithromycin 2'-O-acetate of the general formula (I), wherein $R^1$ and $R^6$ are mutually the same and stand for hydroxid group, $R^3$, $R^7$ and $R^8$ are mutually the same and stand for hydrogen, $R^4$ is acetyl and $R^5$ is methyl, or 3-de(2,6-dideoxy-3-C-methyl-3-O-methyl-α-L-ribohexopyranosyl-oxy)-3-oxy-11-O-methyl-azithromycin 2'-O-acetate of the general formula (I), wherein $R^1$ and $R^6$ are mutually the same and stand for hydroxyl group, $R^3$ and $R^8$ are mutually the same and stand for hydrogen, $R^4$ is acetyl and $R^5$ and $R^7$ are mutually the same and stand for methyl, or 3-de(2,6-dideoxy-3-C-methyl-3-O-methyl-α-L-ribohexopyranosyl-oxy)-3-oxy- 12-O-methyl-azithromycin 2'-O-acetate of the general formula (I), wherein $R^1$ and $R^6$ are mutually the same and stand for bydroxyl group, $R^3$ and $R^7$ are mutually the same and stand for hydrogen, $R^4$ is acetyl and $R^5$ and $R^8$ are mutually the same and stand for methyl.

As suitable bases there are used sodium hydrogen carbonate, sodium carbonate, potassium carbonate, triethylamine, pyridine, tributylamine, preferably sodium hydrogen carbonate. As a suitable inert solvent there is used methylene chloride, dichloroethane, acetone, pyridine, ethyl acetate, tetrahydrofuran, preferably methylene chloride.

Step 7

3-De(2,6-dideoxy-3-C-methyl-3-O-methyl-α-L-ribohexopyranosyl-oxy)-3-oxy-azithromycin 2'-O-acetate and its 11-O-methyl- and 12-O-methyl derivatives from the Step 6 are subjected to oxidation of the hydroxyl group in C-3 position with Jones reagent or diimides according to a modified Moffat-Pfitzner process [DMSO and 1-(3-dimethylaminopropyl)-3-ethyl-carbodiimide in the presence of pyridine trifluoro-acetate] yielding 3-de(2,6-dideoxy-3-C-methyl-3-O-methyl-α-L-ribohexopyranosyl-oxy)-azithromycin 3,6-hemiketal 2'-O-acetate of the general formula (I), wherein $R^1$ stands for hydroxyl group, $R^3$ together with $R^6$ stands for an ether group, $R^4$ is acetyl, $R^5$ is methyl, and $R^7$ and $R^8$ are mutually the same and stand for hydrogen, or 3-de(2,6-dideoxy-3-C-methyl-3-O-methyl-α-L-ribohexopyranosyl-oxy)- 11-O-methyl-azithromycin 3,6-hemiketal 2'-O-acetate of the general formula (I), wherein $R^1$ stands for hydroxyl group, $R^3$ together with $R^6$ stands for an ether group, $R^4$ is acetyl, $R^5$ and $R^7$ are mutually the same and stand for methyl, and $R^8$ is hydrogen, or 3-de(2,6-dideoxy-3-C-methyl-3-O-methyl-α-L-ribo-hexopyranosyl-oxy)-12-O-methyl-azithromycin 3,6-hemiketal 2'-O-acetate of the general formula (I), wherein $R^1$ stands for hydroxyl group, $R^3$ together with $R^6$ stands for an ether group, $R^4$ is acetyl, $R^5$ and $R^8$ are mutually the same and stand for methyl and $R^7$ is hydrogen.

Step 8:

3-De(2,6-dideoxy-3-C-methyl-3-O-methyl-α-L-ribohexopyranosyl-oxy)-azithromycin 3,6-hemiketal 2'-O-acetate and its 11-O-methyl- and 12-O-methyl-derivatives from the Step 7 are subjected to solvolysis in lower alcohols, preferably in methanol, at a temperature from room temperature to the reflux temperature of the solvent, yielding 3-de(2,6-dideoxy-3-C-methyl-3-O-methyl-α-L-ribohexopyranosyl-oxy)-azithromycin 3,6-hemiketal of the general formula (I), wherein $R^1$ stands for hydroxyl group, $R^3$ together with $R^6$ stands for an ether group, $R^4$, $R^7$ and $R^8$ are mutually the same and stand for hydrogen, and $R^5$ is methyl, or 3-de(2,6-dideoxy-3-C-methyl-3-O-methyl-α-L-ribohexopyranosyl-oxy)-1 1-O-methyl-azithromycin 3,6-hemiketal of the general formula (I), wherein $R^1$ stands for hydroxyl group. $R^3$ together with $R^6$ stands for an ether group, $R^4$ and $R^8$ are mutually the same and stand for hydrogen and $R^5$ and $R^7$ are mutually the same and stand for methyl, or 3-de(2,6-dideoxy-3-C-methyl-3-O-methyl-α-L-ribohexopyranosyl-oxy)-12-O-methyl-azithromycin 3,6-hemiketal of the general formula (I), wherein $R^1$ stands for hydroxyl group, $R^3$ together with $R^6$ stands for an ether group, $R^4$ and $R^7$ are mutually the same and stand for hydrogen, and $R^5$ and $R^8$ are mutually the same and stand for methyl.

Step 9

3-De(2,6-dideoxy-3-C-methyl-3-O-methyl-α-L-ribohexopyranosyl-oxy)-azithromycin 3,6-hemiketal from the Step 8 is subsequently optionally subjected to a reaction with ethylene carbonate in the presence of inorganic or organic bases, preferably potassium carbonate, in a reaction-inert solvent, preferably ethyl acetate, yielding 3-de(2,6-dideoxy-3-C-methyl-3-O-methyl-α-L-ribohexopyranosyl-oxy)-azithromycin 3,6-hemiketal 11,12 cyclic carbonate of the general formula (I), wherein $R^1$ stands for hydroxyl group, $R^3$ together with $R^6$ stands for an ether group, $R^4$ is hydrogen, $R^5$ is methyl and $R^7$ and $R^8$ together with C-11 and C-12 carbon atoms stand for a cyclic carbonate.

Pharmaceutically acceptable addition salts, which are another object of the present invention, are obtained by a reaction of the novel compounds of the general formula (I) with an at least equimolar amount of a corresponding inorganic or organic acid such as hydrochloric, hydroiodic, sulfuric, phosphoric, acetic, propionic, trifluoroacetic, maleic, citric, stearic, succinic, ethylsuccinic, methanesulfonic, benzene-sulfonic, p-toluenesulfonic, laurylsulfonic and similar acids, in a reaction-inert solvent. The addition salts are isolated by filtration if they are insoluble in the reaction-inert solvent, by precipitation with a nonsolvent or by evaporation of the solvent, most frequently by lyophilization.

Antibacterial in vitro activity of the novel compounds of the general formula (I) and their pharmaceutically acceptable addition salts with inorganic or organic acids on a series of standard test-microorganisms was determined in a Mueller-Hinton medium (Difco-Laboratories, Detroit, Mich.) by a conventional method of double dilution in accordance with recommendations of NCCLS (The National Committee for Clinical Laboratory Standards). Each test microorganism was inoculated to the final inoculum size of $5\times10^5$ cfu/ml and the incubation was carried out in an anaerobic manner at 37° C. during 18 hours. The MIC in the liquid medium was defined as the lowest concentration of an antibacterial agent inhibiting visible growth in microdilutional containers. Control organisms were obtained from ATCC (The American Type Culture Collection). All standards were identified by a standard procedure and were storaged at −70° C. The results of 12-O-methyl-azithromycin on standard test microorganisms and clinical isolates in comparison with azithromycin are shown in Table 1 and Table 2.

By determining the concentration of 12-O-methyl-azithromycin in serum after a single oral dosis of 20 mg/kg on a group of 36 male rats in time intervals from 0.25 to 24 hours it was established that the novel antibiotic was very fast absorbed in the serum. An analysis of the peaks suggested the existence of enterohepatic circulation. During 0.5 and 1 hours a rapid drop of concentration took place, which was followed by a repeated increase. The maximum substance concentration was achieved after 2 hours (Cmax 248.8 ng/ml). A secondary maximum was achieved 4 hours after the application. The half-life was 5.2 hours and the total AUC was 1993.4 h ng/ml.

TABLE 1

Antibacterial in vitro activity of 12-O-methyl-azithromycin on standard strains in comparison with azithromycin

| | MIC (mcg/ml) | |
|---|---|---|
| Organism | Azithromycin | 12-O-Methyl-azithromycin |
| Staphylococcus aureus ATCC 6538 P | 1 | 0.25 |
| S. aureus ATCC 29213 | 0.25 | 0.25 |
| S. eperidermidis ATCC 12228 | 0.5 | 0.03 |
| Micrococcus flavus ATCC 10240 | 0.5 | 0.12 |
| M. luteus ATCC 9341 | 0.06 | 0.03 |
| Streptococcus faecalis ATCC 8043 | 0.5 | 0.25 |
| Bacillus subtilis ATCC 6633 | 4 | 1 |
| B. cereus ATCC 11778 | 1 | 0.25 |
| Escherichia coli ATCC 10536 | 1 | 0.5 |

TABLE 2

Antibacterial in vitro activity of 12-O-methyl-azithromycin on a series of clinical isolates in comparison with azithromycin

| Organism | | MIC ($\mu$g/ml) | | |
|---|---|---|---|---|
| (No. of strains) | Compound | Range | 50% | 90% |
| Staph. aureus. | Azithromycin | 0.25–8 | 1 | 4 |
| (77) | 12-O-Methylazithromycin | 0.12–2 | 0.25 | 1 |
| S. epidermidis | Azithromycin | 0.25–16 | 0.25 | 8 |
| (20) | 12-O-Methylazithromycin | 0.12–8 | 0.25 | 4 |
| Streptococcus | Azithromycin | 0.03–0.25 | 0.05 | 0.12 |
| pneumoniae | 12-O-Methylazithromycin | 0.03–0.12 | 0.03 | 0.12 |
| (25) | | | | |
| Enterococcus sp. | Azithromycin | 0.25–16 | 1 | 16 |
| (35) | 12-O-Methylazithromycin | 0.12–8 | 0.5 | 8 |
| Haemophilus | Azithromycin | 0.12–0.5 | 0.25 | 0.5 |
| influenzae | 12-O-Methylazithromycin | 0.06–0.5 | 0.12 | 0.25 |
| (40) | | | | |

The process for the preparation of novel 3,6-hemiketals from the class of 9a-azalides is illustrated by the following examples, which in no way limit the scope of the invention.

Preparation 1

2'-O,3'-N-Bis(bezyloxyearbonyl)-3'-N-demethyl-azithromycin A

To a solution of azithromycin (17 g, 0.0227 mole) in toluene (170 ml), NaHCO$_3$ (74.8 g, 0.890 mole) was added and then the reaction mixture was heated under stirring to reflux temperature (80–85° C.). To the reaction suspension 102 ml of 50% benzyloxy-carbonyl chloride (104.04 g, 0.305 mole) in toluene were added dropwise under stirring during 1 hour. The reaction mixture was stirred at the same temperature for furher 2 hours and left standing over night at room temperature. After filtration the precipitate was rinsed with toluene (85 ml) and the toluene solution was extracted twice with 0.25 N HCl (170 ml) and twice with 1.5% aqueous NaCl solution (170 ml). To toluene water was added (340 ml) (pH 3.1), the pH of the reaction mixture was adjusted with 6 N HCl to 2.0, the layers were separated and the organic layer was further extracted three times with water (340 ml) under keeping the pH at 2.0. To combined water extracts CH$_2$Cl$_2$ (125 ml) was added, the pH was adjusted with an aqueous NaOH solution (20%) to 10, the layers were separated and the aqueous layer was again extracted with CH$_2$Cl$_2$ (125 ml). The combined organic extracts were dried over K$_2$CO$_3$, filtered and evaporated at a reduced pressure, yielding 16.5 g of a thick oily residue, which was optionally purified with low-pressure chromatography on a silica gel 60 column (230–400 mesh ASTM). For this purpose the crude product was dissolved in CH$_2$Cl$_2$ (20 ml) and applied to a silica gel column (50 g) under nitrogen pressure of 0.5 bar. In order to remove the residual benzylchloroformate and its disintegration products, CH$_2$Cl$_2$ (150 ml) was led through the column and then by using the solvent system methylene chloride-methanol, 9:1 (200 ml) and evaporating the fractions containing chromatographically homogeneous title product, there were obtained 11.53 g of TLC pure 2'-O,3'-N-bis-(benzyloxycarbonyl)-N-demethyl-azitruomycin with physical-chemical constants as described in U.S. Pat. No. 5,250,518 of October 1993.

EXAMPLE 1

4",11-O-Bis(trimethylsilyl)-2'-O,3'-N-bis (benzyloxycarbonyl)-3'-N-demethyl-azithromycin To a solution of 2'-O,3'-N-bis(benzyloxycarbonyl)-3'-N-demethyl-azithromycin (5.0 g, 0.005 mole) in pyridine (50 ml), cooled to 0–5° C., trimethylsilylimidazole (3.3 ml, 0.0226 mole) and trimethylsilylchloride (3.0 ml, 0.0179 mole) were added under nitrogen stream. The reaction mixture was stirred at the same temperature for 6 hours, n-hexane (60 ml) and water (100 ml) were added, the layers were separated and the organic layer was rinsed with a saturated NaHCO$_3$ solution (60 ml) and water (60 ml). After drying over MgSO$_4$, filtration and evaporation of the solvent at a reduced pressure, 5.48 g of a white amorphous precipitate were obtained, which were optionally purified by low-pressure chromatography on a silica gel column using the system CH$_2$Cl$_2$—CH$_3$OH, 9:1. The combining and evaporation of chromatographically homogeneous fractions gave the title product with the following physical-chemnical constants:

| TLC, | Methylene chloride-methanol, 90:1 | Rf 0.875 |
|---|---|---|
| | Ethyl acetate-N-hexane-diethyl amine, 100:100:20 | Rf 0.942 |

(IR (KBr) cm$^{-1}$: 3524, 2969, 2692, 1754, 1732, 1708, 1498, 1456, 1382, 1335, 1252, 1168, 1116, 1060, 1005, 895, 841, 754, 696.

$^1$H NMR(300 MHz, CDCl$_3$) $\delta$: 7.32–7.23 (Ph), 5.12, 4.98 (CH$_2$—Ph), 4.85 (H-1"), 4.70 (H-1'), 4.65 (H-2'), 4.46 (H-3'), 4.26 (H-5"), 4.42 (H-3), 3.72 (H-5'), 3.66 (H-11) 3.49, 3.47 (H-5), 3.20 (H-4"), 3.32, 3.18 (3"-OCH$_3$), 2.83, 2.79 (3'-NCH$_3$), 2.7 (H-2), 2.64 (H-10), 2.35 (H-9a), 2.33 (H-2"a), 2.11 (9a-NCH$_3$), 1.94 (H-9b), 1.91 (H-8), 1.64 (H-14a), 1.94 (H-4), 1.50 (H-2"b), 1.50 (H-14b), 1.27, 1.25 (6-CH$_3$), 1.24 (5"-CH$_3$), 1.19 (5'-CH$_3$), 1.12 (3"-CH$_3$), 1.16 (12-CH$_3$), 1.26 (2-CH$_3$), 0.89 (10-CH$_3$), 0.95 (8-CH$_3$), 0.85 (14-CH$_3$), 1.02 (4-CH$_3$), 1.02 (4-CH$_3$), 0.16 (11-OSi(CH$_3$)$_3$, and 0.13 /4"-OSi(CH$_3$)$_3$/.

$^{13}$C NMR (75 MHz, CDCl$_3$) $\delta$: 176.2 (C-1), 156.2, 156.4 (OCO), 154.5, 154.4 (NCO), 136.7-127.5 (Ph), 100.2 (C-1'), 97.3 (C-1"), 83.9 (C-5), 80.7 (C-4"), 75.0 (C-3), 75.0 (C-2'), 75.3 (C-6), 73.2 (C-3"), 69.4, 69.2, 67.1, 66.8 (CH$_2$—Ph), 64.8 (C-5"), 62.3 (C-10), 54.8 (C-3'), 49.4, 49.2 (3"-OCH$_3$), 46.2 (C-2), 38.5 (C-7), 39.4 (C-4), 34.2 (9a-NCH$_3$), 35.9, 35.6 (C-2"), 36.2, 36.1 (C-4'), 29.0 (3'-NCH$_3$), 25.6 (C-8), 27.8 (6-CH$_3$), 21.9 (3"-CH$_3$), 21.5 (8-CH$_3$), 20.7 (5'-CH$_3$), 23.4 (C-14), 18.4 (5"-CH$_3$), 16.0 (2-CH$_3$), 11.6 (14-CH$_3$), 9.6, 9.5 (4-CH$_3$), 8.3 (10-CH$_3$), 1.2 /11-OSi(CH$_3$)/$_3$ and 0.67/4"-OSi(CH$_3$)$_3$/.

ES-MS 1147

EXAMPLE 2

3'-N-Demethyl-12-O-methyl-azithromycin

To a solution of the product from Example 1 (1.0 g, 0.0009 mole) in N,N-dimethyl-formamide (20 ml) methyl iodide (0.43 ml, 0.0069 mole) and 60% sodium hydride (0.23 g, 0.0058 mole) were gradually added during 3 hours at room temperature. The reaction mixture was stirred for further 30 minutes at the same temperature, the reaction was stopped by the addition of triethyl amine (2 ml), it was transferred into a mixture of 10% aqueous $NaHCO_3$ solution (50 ml) and water (50 ml) and extracted with ethyl acetate. The combined organic extracts were rinsed with a saturated NaCl solution and water, dried over $MgSO_4$, filtered and evaporated at a reduced pressure, yielding 0.93 g of a yellow precipitate [Rf 0.832, methylene chloride-methanol, 90:1; IR(KBr)cm$^{-1}$: 3516, 1752, 1732, 1705, 1456, 1382, 1336, 1253, 1169, 1116, 1062, 1004, 896, 840, 754, 696]. The product was dissolved in ethanol (20 ml), NaOAc/HOAc buffer with pH 5 (0.17 ml acetic acid, 0.263 g sodium acetate, 0.22 ml ethanol and 1 ml water) and Pd/C 10% (0.6 g) were added, and the reaction mixture was hydrogenated under stirring for 5 hours in an autoclave at a hydrogen pressure of 5 bars, The catalyst was filtered off, the filtrate was evaporated to a thick syrup, $CH_2Cl_2$ (10 ml) and water (15 ml) were added, the pH of the mixture was adjusted with 2 N HCl to 4, the layers were separated and the aqueous layer was, upon adjustment to pH 9.5 with 20% NaOH, extracted with $CH_2Cl_2$ (3×10 ml). The combined organic extracts were dried over $K_2CO_3$, filtered and evaporated. The precipitate was dissolved in isopropanol (10 ml), water (10 ml) and some drops of formic acid were added and it was stirred for 30 minutes at room temperature, extracted with isopropyl acetate at pH 9.5, which upon evaporation at a reduced pressure yielded 0.43 g of the title product with the following physical-chemical constants:

IR (KBr) cm$^{-1}$: 3672, 3496, 2962, 1727, 1458, 1375, 1343, 1280, 1263, 1118, 1085, 1048, 1005, 998.

$^{13}$C NMR (75 MHz, CDCl$_3$) δ: 177.4 (C-1), 102.7 (C-1'), 95.5 (C-1"), 83.4 (C-5), 79.7 (C-12), 78.0 (C-3), 76.6 (C-11), 74.0 (C-13), 73.9 (C-6), 74.3 (C-2'), 73.0 (C-3"), 68.8 (C-9), 65.7 (C-5"), 60.1 (C-3'), 61.2 (C-10), 52.8 (12-OCH$_3$), 49.8 (3"-OCH$_3$), 45.5 (C-2), 41.5 (C-4), 33.1, 3'-NCH$_3$, 36.8 (9a-NCH$_3$), 35.1 (C-2"), 28.8 (C-4'), 27.0 (C-8).

EI-MS m/z 748.

Example 3

12-O-Methyl-azithromycin

To a solution of 3'-N-demethyl-12-O-methyl-azithromycin from Example 2 (0.43 g, 0.0006 mole) in CHCl$_3$ (20 ml), formaldehyde (37%) (0.047 ml, 0.0006 mole) and formic acid (98–100%) (0.042 ml, 0.0011 mole) were added. The reaction mixture was stirred for 3 hours under reflux, cooled to room temperature, poured onto water (20 ml) and upon adjustment of pH to 4.0, the layers were separated and the aqueous layer was extracted two more times with CHCl$_3$. To the aqueous layer CHCl$_3$ was added, the pH was adjusted to 9.5 (2N NaOH), the layers were separated and the aqueous one was extracted two more times with CHCl$_3$. The combined organic extracts at pH 9.5 were dried (K$_2$CO$_3$) and evaporated, yielding 0.38 g of the title product, which was, if necessary, purified by a chromatography on a silica gel column using the system $CH_2Cl_2$—$CH_3OH$-conc.$NH_4OH$, 90:9:1.

| TLC, | Methylene chloride-methanol-conc. ammonia, 90:9:0.5 | Rf 0.363 |
|---|---|---|
| | Ethyl acetate-N-hexane-diethyl amine, 100:100:20 | Rf 0.745 |

IR (KBr) cm$^{-1}$: 3499, 2972, 2940, 1736, 1633, 1460, 1381, 1259, 1168, 1110, 1059, 1082, 1054, 1013, 999.

$^1$H NMR (300 MHz, CDCl$_3$) δ: 5.39 (H-13), 5.00 (H-1"), 4.43 (H-1'), 4.32 (H-3), 4.06 (H-5"), 3.68 (H-11), 3.65 (H-5), 3.51 (H-5'), 3.38 (12-OCH$_3$), 3.32 (3"-OCH$_3$), 3.24 (H-2'), 3.02 (H-4"), 2.73 (H-2), 2.69 (H-10), 2.49 (H-3'), 2.34 (H-2"a), 2.31 (H-9a), 2.29 /3'N(CH$_3$)$_2$/, 2.30 (9a-NCH$_3$), 2.12 (H-9b), 2.04 (H-4), 2.01 (H-8), 1.73 (H-14a), 1,68 (H-4'a), 1.66 (H-7a), 1.56 (H-2"b), 1.52 (H-14b), 1.36 (H-7b), 1.29 (6-CH$_3$), 1.21 (2-CH$_3$), 1.30 (5"-CH$_3$), 1.24 (H-4'b), 1.23 (3"-CH$_3$), 1.22 (5'-CH$_3$), 1.09 (12-CH$_3$), 1.29 (4-CH$_3$), 1.09 (10-CH$_3$), 0.92 (8-CH$_3$), 0.93 (14-CH3).

$^{13}$C NMR (75 MHz, CDCl$_3$) δ177.5 (C-1), 103.1 (C-1'), 95.2 (C-1"), 83.6 (C-5), 79.2 (C-12), 78.1 (C-3), 76.6 (C-11), 74.7 (C-13), 73.8 (C-6), 70.9 (C-2'), 68.8 (C-9), 65.6 (C-5"), 65.7 (C-3'), 61.6 (C-10), 52.8 (12-OCH$_3$), 49.4 (3"-OCH$_3$), 45.1 (C-2), 43.0 (C-7), 41.8 (C-4), 40.4 /3'N(CH$_3$)$_2$/, 36.8 (9a-NCH$_3$), 35.0 (C-2"), 29.0 (C-4'), 26.9 (C-8), 26.9 (6-CH$_3$), 22.0 (8-CH$_3$), 22.0 (C-14), 21.6 (3"-CH$_3$), 21.3 (5'-CH$_3$), 18.1 (5"-CH$_3$), 16.9 (12-CH$_3$), 14.6 (2-CH$_3$), 11.0 (14-CH$_3$), 9.6 (4-CH$_3$), 9.4 (10-CH$_3$).

EXAMPLE 4

3-De(2,6-dideoxy-3-C-methyl-3-O-methyl-α-L-ribohexopyranosyl-oxy)-3-oxy-12-O-methyl-azithromycin In 0.25 N hydrochloric acid (80 ml) 12-O-methyl-azithromycin (1.7 g, 0.0022 mole) from Example 3 was dissolved and it was left standing for 24 hours at room temperature. To the reaction mixture $CH_2Cl_2$ (pH 1.8) was added, the layers were separated and the aqueous one was extracted two more times with $CH_2Cl_2$. To the aqueous layer again $CH_2Cl_2$ was added, the pH of the rmixture was adjusted with conc. $NH_4OH$ to 9.0, the layers were separated and the aqueous one was extracted with $CH_2Cl_2$. The combined organic extracts at pH 9.0 were rinsed with 10% aqueous $NaHCO_3$ solution and water, dried over $K_2CO_3$ and evaporated, yielding 1.25 g of the title product with the following physical-chemical constants:

| TLC, | Methylene chloride-methanol-conc. ammonia, 90:9:0.5 | Rf 0.315 |
|---|---|---|
| | Ethyl acetate-N-hexane-diethyl amine, 100:100:20 | Rf 0.594 |

IR (KBr) cm$^{-1}$: 3450, 2971, 2933, 1711, 1648, 1460, 1381, 1272, 1261, 1171, 1113, 1078, 1049.

$^1$H NMR (300 MHz, CDCl$_3$) δ: 5.32 (H-13), 4.47 (H-1'), 3.78 (H-3), 3.66 (H-11), 3.58 (H-5), 3.58 (H-5'), 3.41 (12-OCH$_3$), 3.28 (H-2'), 2.67 (H-2), 2.80 (H-10), 2.35 (H-3'), 2.53 (H-9a), 2.27 /3'N(CH$_3$)$_2$/, 2.37 (9a-NCH$_3$), 2.07 (H-9b), 2,27 (H-4), 1.92 (H-8), 1.74 (H-14a), 1.68 (H-4'a), 1.59 (H-7a), 1.63 (H-14b), 1.51 (H-7b), 1.31 (6CH$_3$), 1.31 (2-CH$_3$), 1.29 (H-4'b), 1.26 (5'-CH$_3$), 1.08 (12-CH$_3$), 1.05 (4-CH$_3$), 1.19 (10-CH$_3$), 0.93 (8-CH$_3$), 0.92 (14-CH$_3$).

$^{13}$C NMR (75 MHz, CDCl$_3$) δ: 177.2 (C-1), 106.4 (C-1'), 94.7 (C-5), 78.0 (C-12), 79.0 (C-3), 78.3 (C-11), 75.1 (C-13), 72.9 (C-6), 70.2 (C-2'), 70.3 (C-9), 65.3 (C-3'), 62.1 (C-10), 52.5 (12-OCH$_3$), 44.3 (C-2), 41.8 (C-7), 35.7 (C-4), 39.9 /3'N(CH₃)₂/, 36.5 (9a-NCH₃), 27.9 (C-4'), 26.4 (C-8), 25.5 (6-CH₃), 20.8 (8-CH₃), 20.7 (C-14), 20.8 (5'-CH₃, 16.1 (12-CH₃), 15.7 (2-CH₃), 10.3 (14-CH₃), 7.6 (4-CH₃), 7.2 (10-CH₃).

EXAMPLE 5

3-De(2,6-dideoxy-3-C-methyl-3-O-methyl-δ-L-ribohexopyranosyl-oxy)-3-oxy-12-O-methyl-azithromycin-2'-O-acetate To a solution of 3-de(2,6-dideoxy-3-C-methyl-3-O-methyl-α-L-ribohexopyranosyl-oxy)-3-oxy-12-O-methyl-azithromycin (1.3 g, 0.0022 mole) from Example 4 in CH₂Cl₂ (20 ml), NaHCO₃ (0.754 g, 0.009 mole) and acetic acid anhydride (0.221 ml, 0.0023 mole) were added and then it was stirred for 10 hours at room temperature. After standing over night saturated NaHCO₃ solution was added to the reaction mixture, the layers were separated and the aqueous one was extracted with CH₂Cl₂. The combined organic extracts were rinsed with a saturated NaHCO₃ solution and water, dried over K₂CO₃, filtered and evaporated, yielding 1.29 g of a white amorphous precipitate.

| TLC, | Methylene chloride-methanol-conc. ammonia, 90:9:0.5 | Rf 0.489 |
|---|---|---|
| | Ethyl acetate-N-hexane-diethyl amine, 100:100:20 | Rf 0.661 |

IR (KBr) cm⁻¹: 3448, 2974, 1749, 1718, 1637, 1458, 1377, 1242, 1169, 1115, 1045.

¹H NMR (300 MHz, CDCl₃) δ: 5.23 (H-13), 4.72 (H-2'), 4.70 (H-1'), 3.59 (H-11), 3.56 (H-5), 3.52 (H-3), 3.43 (H-5'), 3.33 (12-OCH₃), 2.72 (H-10), 2.71 (H-3'), 2.61 (H-2), 2.42 (H-9a), 2.30 (9a-NCH₃), 2.20 /3'N(CH₃)₂/, 2.12 (H-4, 1.99 (2'-COCH₃), 1.96 (H-9b), 1.80 (H-8), 1.67 (H-14a), 1.67 (H-4'a), 1.58 (H-14b), 1.47 (H-7a), 1.31 (H-4'b), 1.21 (2-CH₃), 1.18 (H-7b), 1.16 (5'-CH₃), 1.15 (6-CH₃), 1.10 (10-CH₃), 0.97 (12-CH₃), 0.86 (14-CH₃), 0.84 (8-CH₃), 0.81 (4-CH₃).

¹³C NMR (75 MHz, CDCl₃) δ: 176.5 (C-1), 169.4 (2'-COCH₃), 98.6 (C-1'), 84.3 (C-5), 77.3 (C-12), 78.3 (C-3), 76.7 (C-11), 74.6 (C-13), 72.4 (C-6), 70.7 (C-2'), 69.9 (C-9), 62.2 (C-3'), 62.3 (C-10), 51.9 (12-OCH₃), 43.0 (C-2), 40.1 (C-7), 35.2 (C-4), 39.6 /3'N(CH₃)₂/, 35.9 (9a-NCH₃), 30.0 (C-4'), 25.4 (C-8), 25.2 (6-CH₃), 20.6 (2'COCH₃), 20.4 (8-CH₃), 20.0 (C-14), 20.2 (5'-CH₃), 15.9 (12-CH₃), 15.2 (2-CH₃), 9.7 (14-CH₃), 7.0 (4-CH₃), 6.4 (10-CH₃).

EXAMPLE 6

3-De(2,6-dideoxy-3-C-methyl-3-O-methyl-α-L-ribohexyopyranosyl-oxy)-12-O-methyl-azithromycin 3,6-hemiketal-2'-O-acetate To a solution of 3-de(2,6-dideoxy-3-C-methyl-3-O-methyl-δ-L-ribohexopyranosyl-oxy)-3-oxy-12-O-methyl-azithromycin 2'-O-acetate (1.3 g, 0.0020 mole) from Example 5 in CH₂Cl₂ (15 ml), dimethyl sulfoxide (4.35 ml) and N,N-dimethyl-amino-propyl-ethyl-carbodiimide (4.55 g) were added. The reaction mixture was cooled to 15° C. and then under stirring and keeping the temperature at 15° C. a solution of pyridirium trifluoroacetate (4.61 g, 0.0234 mole) in CH₂Cl₂ (10 ml) was added dropwise over 30 minutes. The temperature of the reaction mixture was gradually increased to room temperature and it was stirred for further 2 hours, whereupon the reaction was stopped by the addition of a saturated NaCl solution (25 ml). After alkalizing with 2 N NaOH to 9.5, the reaction mixture was extracted with CH₂Cl₂, the organic extracts were rinsed with a saturated NaCl solution, NaHCO₃ and water and dried over K₂CO₃. The evaporation of CH₂Cl₂ at a reduced pressure gave 1.78 g of an oily residue.

| TLC, | Methylenechloride-methanol-conc. ammonia, 90:9:0.5 | Rf 0.176 |
|---|---|---|
| | Ethyl acetate-N-hexane-diethyl amine, 100:100:20 | Rf 0.861 |

EXAMPLE 7

3-De(2,6-dideoxy-3-C-methyl-3-O-methyl-α-L-ribohexopyranosyl-oxy)-12-O-methyl-azithromycin 3,6-hemiketal A solution of 3-de(2,6-dideoxy-3-C-methyl-3-O-methyl-(α-L-ribohexopyranosyl-oxy)-12-O-methyl-azithromycin 2'-O-acetate (1.78 g) from Example 6 in methanol (50 ml) was left standing for 24 hours at room temperature. Methanol was evaporated at a reduced pressure, the obtained residue (1.65 g) was purified by low-pressure chromatography on a silica gel column using the system methylene chloride-methanol-conc. ammonia, 90:9:0.5. By evaporating the combined extracts with Rf 0.082 there was obtained chromatographically homogeneous 3-de(2,6-dideoxy-3-C-methyl-3-O-methyl-δ-L-ribohexopyranosyl-oxy)-12-O-methyl-azithromycin-3,6-herniketal with the following physical-chemical constants:

| TLC, | Methylene chloride-methanol-conc. ammonia, 90:9:0.5 | Rf 0.082 |
|---|---|---|
| | Ethyl acetate-N-hexane-diethyl amine, 100:100:20 | Rf 0.624 |

IR (CDCl₃) cm⁻¹: 3450, 2956, 2940, 1718, 1678, 1631, 1459, 1383, 1278, 1198, 1117, 1068, 1048, 1014, 963.

¹H NMR (300 MHz, CDCl₃) δ: 5.49 (H-13), 4.21 (H-1'), 3.83 (H-11), 3.75 (H-5),3.52 (H-5'), 3.43 (12-OCH₃), 3.25 (H-2'), 2.59 (H-2), 2.93 (H-10), 2.50 (H-3'), 2.61 (H-9a), 2.29 /3'N(CH₃)₂/, 2.40 (9a-NCH₃), 2.10 (H-9b), 2.06 (H-4), 1.88 (H-8), 1.77 (H-14a), 1.67 (H-4'a), 1.61 (H-7a), 1.64 (H-14b), 1.33 (H-7b), 1.31 (6-CH₃), 1.05 (2-CH₃), 1.27 (H-4'b), 1.26 (5'-CH₃), 1.08 (12-CH₃), 1.05, (4-CH₃), 1.19 (10-CH₃), 0.92 (8-CH₃), 0.93 (14-CH₃).

¹³C NMR (75 MHz, CDCl₃) δ: 176.2 (C-1), 105.8 (C-1'), 94.6 (C-5), 78.3 (C-12), 102.7 (C-3), 71.2 (C-11), 74.8 (C-13), 82.9 (C-6), 69.6 (C-2'), 64.5 (C-9), 65.1 (C-3'), 60.7 (C-10), 52.2 (12-OCH₃), 49.2 (C-2), 41.4 (C-7), 48.6 (C-4), 40.0 /3'N(CH₃)₂/, 40.5 (9a-NCH₃), 28.2 (C-4'), 29.1 (C-8), 26.5 (6-CH₃), 21.5 (8-CH₃), 21.6 (C-14), 20.8 (5'-CH₃), 16.3 (12-CH₃), 13.6 (2-CH₃), 10.7 (14-CH₃), 12.8 (4-CH₃), 10.7 (10-CH₃).

EXAMPLE 8

4"-O-Trimethylsilyl-2'-O-3'-N-bis(benzyloxycarbonyl)-3'-N-demethyl-azithromycin

To a solution of 2'-O,3'-N-bis(benzyloxycarbonyl)-3'-N-demethyl-azithromycin (5 g, 0.005 mole) in pyridine (30 ml) cooled to 0–5° C., trimethylsilyl imidazole (1.46 ml, 0.01 mole) and trimethylsilyl chloride (1.64 ml, 0.01 mole) were added under a nitrogen stream. The reaction mixture was stirred for 1 hour at the same temperature, n-hexane (50 ml) and water (25 ml) were added, the layers were separated and the organic one was rinsed with a saturated NaHCO$_3$ solution (25 ml) and water (25 ml). After drying over MgSO$_4$, filtration and evaporation of the solvent at a reduced pressure there was obtained an amorphous precipitate (3.65 g), which was optionally purified by low-pressure chromatography on a silica gel column using the system methylene chloride-methanol-conc. ammonia, 90:9:0.5. By combining and evaporating the chromatographically homogeneous fractions with Rf 0.670 there was obtained the title product with the following physical-chemical constants:

| TLC, | Methylene chloride-methanol, 90:1 | Rf 0.525 |
|---|---|---|
| | Ethyl acetate-N-hexane-diethyl amine, 100:100:20 | Rf 0.862 |

IR (KBr) cm$^{-1}$: 3502, 2969, 2938, 1753, 1732, 1708, 1454, 1383, 1365, 1254, 1169, 1118, 1063, 1001, 897, 839, 754, 696.

$^1$H NMR (300 MHz, CDCl$_3$) δ: 7.34–7.26 (Ph), 5.13, 5.09, (CH$_2$—Ph), 5.07 (H-1"), 4.78 (H-1'), 4.68 (H-13), 4.66 (H-2'), 4.55 (H-3'), 4.22 (H-5"), 4.13 (H-3), 3.96 (H-5'), 3.65 (H-11), 3.58, 3.54 (H-5), 3.15 (H-4"), 3.37, 2.99 (3"-OCH$_3$), 2.85, 2.81 (3'-NCH$_3$), 2.70 (H-2), 2.68 (H-10), 2.54 (H-9a), 2.35 (H-2"a), 2.31 (9a-NCH$_3$), 2.04 (H-9b), 1.97 (H-8), 1.90 (H-14a), 1.85 (H-4), 1.62 (H-7a), 1.50 (H-2"b), 1.44 (H-14b), 1.28, 1.27 (6-CH$_3$), 1.23 (5"-CH$_3$), 1.16 (5'-CH$_3$), 1.15 (H-7b), 1.04 (3"-CH$_3$), 1.15 (12-CH$_3$), 1.10 (2-CH$_3$), 1.10 (10-CH$_3$), 0.92 (8-CH$_3$), 0.89 (14-CH$_3$), 1.10 (4-CH$_3$).

$^{13}$C NMR (75 MHz, CDCl$_3$) δ: 178.8 (C-1), 156.6, 156,3 (OCO), 154.7, 154.6 (NCO), 136.8–127-5 (Ph), 99.2 (C-1'), 94.8 (C-1'"), 83.2, 83.1 (C-5), 80.5, 80.4 (C-4"), 77.3 (C-3), 75.1, 75.0 (C-2'), 74.1 (C-12), 73.8 (C-11), 73.2 (C-6), 73.2 (C-3 "), 69.2, 69.0 67.2, 66.8 (CH$_2$-Ph), 64.8 (C-5"), 62.2 (C-10), 54.6 (C-3'), 49.3, 48.8 (3"-OCH$_3$), 44.7 (C-2), 41.5 (C-7), 41.1 (C-4), 36.1 (9a-NCH$_3$), 35.1, 35.0 (C-2"), 36.3, 35.7 (C-4'), 28.4 (3'-NCH$_3$), 26.3 (C-8), 26.8 (6-CH$_3$), 22.1 (3"-CH$_3$), 21.6 (8-CH$_3$), 21.4 (5'-CH$_3$), 21.0 (C-14), 18.7 (5"-CH$_3$), 15.9 (2-CH$_3$), 14.5 (12-CH$_3$), 11.0 (14-CH$_3$), 8.5 (4-CH$_3$), 7.1 (10-CH$_3$), 0.63/4"-OSi(CH$_3$)$_3$/.

ES-MS 1075.

EXAMPLE 9

11-O-methyl-azithromycin and 12-O-methyl azithromycin

To a solution of the product from Example 8 (3.0 g, 0.0028 mole) in N,N-dimethylformamide (50 ml), methyl iodide (1.29 ml, 0.0207 mole) and 60% sodium hydride (0.69 g, 0.0174 mole) were gradually added over 3 hours at room temperature. The reaction mixture was stirred for 1 hour at the same temperature, the reaction was stopped by addition of triethylamine (5 ml), it was transferred into a mixture of 10% aqueous NaHCO$_3$ solution (100 ml) and water (100 ml) and extracted with ethyl acetate. The combined organic extracts were rinsed with a saturated NaCl solution and water and dried over MgSO$_4$, filtered and evaporated at a reduced pressure yielding 2.9 g of a mixture of products, which was optionally purified by low-pressure chromatography on a silica gel column using the system methylene chloride-methanol, 90:1, yielding a chromatographically homogeneous 4"-O-trimethylsilyl-2'-O-3'-N-bis(benzyloxy-carbonyl)-3'-N-demethyl-11-O-methyl-azithromycin with Rf 0.745 [IR (KBr): 3452, 2969, 1752, 1736, 1706, 1455, 1382, 1332, 1254, 1169, 1117, 1063, 1002, 914, 897, 840, 754, 697] and 4"-O-trimethylsilyl-2'-O-3'-N-bis(benzyloxy-carbonyl)-3'-N-demethyl-12-O-methyl-azithroinycin with Rf 0.485 [IR (KBr): 3450, 2958, 1754, 1718, 1708, 1458, 1383, 1252, 1168, 1068, 1010, 896, 842, 753, 695].

The obtained mixture was dissolved in ethanol (50 ml), NaOAc/HOAc buffer with pH 5 (0.51 ml HOAc, 0.789 g NaOAc, 0.66 ml ethanol and 3 ml water) and 10% Pd/C (1.5 g) were added and the mixture was hydrogenated under stining for 8 hours in an autoclave at a hydrogen pressure of 5 bars. The catalyst was filtered off, the filtrate was evaporated to a thick syrup, water (50 ml) and CHCl$_3$ (50 ml) were added and the product was isolated by a pH gradient extraction at pH 4.0 and 9.5. The combined organic extracts at pH 9.5 were dried over K$_2$CO$_3$ and evaporated to an amorphous precipitate. The precipitate was dissolved in isopropanol (20 ml), water (20 ml) and some drops of formic acid were added and it was stirred for 30 minutes at room temperature, extracted with isopropyl acetate at pH 9.5, dried over sodium sulfate and evaporated at a reduced pressure. The obtained product was dissolved in CHCl$_3$ (50 ml), formaldehyde (37%) (0.24 ml) and formic acid (98–100%) (0.22 ml) were added. The reaction mixture was stirred for 3 hours under reflux, cooled to room temperature, poured onto water (20 ml) and after adjusting the pH to 4.0 the layers were separated and the aqueous one was extracted two more times with CHCl$_3$. To the water layer CHCl$_3$ was added, pH was adjusted to 9.5 (2 N NaOH), the layers were separated and the aqueous one was extracted two more times with CHCl$_3$. The combined organic extracts at pH 9.5 were dried (K$_2$CO$_3$) and evaporated, yielding 1.25 g of a precipitate, which was chromatographed on a silica gel column using the system methylene chloride-methanol-conc. ammonia, 90:9:1, yielding 0.40 g of chromatographically homogeneous 11-O-methyl-azithromycin with physical-chemical constants as given in U.S. Pat. No. 5,250,518 of October 1993 and 0.52 g of 12-O-methyl-azithromycin with physical-chemical constants as given in Example 3.

EXAMPLE 10

3-De(2,6-dideoxy-3-C-methyl-3-O-methyl-α-L-ribohexopyranosyl-oxy)-3-oxy-11-O-methyl-azithromycin In methanol (30 ml) 11-O-methyl-azithromycin (1.5 g) was dissolved, 0.25 N hydrochloric acid (50 ml) was added and it was left standing for 24 hours at room temperature. Methanol was evaporated, to the reaction mixture CDCl$_3$ (pH 1.9) was added, the layers were separated and the aqueous one was extracted two more times with CDCl$_3$. The aqueous solution was alkalized to pH 9.5 and extracted with CDCl$_3$ The combined organic exctracts at pH 9.5 were dried over K$_2$CO$_3$ and evaporated, yielding 0.95 g of the title product, which was optionally purified by low-pressure chromatography on a silica gel column using the solvent system methylene chloride-methanol-conc. ammonia, 90:9:0.5, yielding a chromatographically homogeneous title product with the following physical-chemical constants:

| TLC, | Methylene chloride-methanol-conc. ammonia, 90:9:0.5 | Rf 0.382 |
|---|---|---|
| | Ethyl acetate-N-hexane-diethyl amine, 100:100:20 | Rf 0.594 |

IR (KBr) cm$^{-1}$: 3448, 2972, 2937, 1730, 1638, 1458, 1377, 1165, 1113, 1078, 1050.

¹H NMR (300 MHz, CDCl$_3$) δ: 4.97 (H-13), 4.52 (H-1'), 3.76 (H-3), 3.70 (11-OCH$_3$), 3.59 (H-5), 3.54 (H-5'), 3.42 (H-11), 3.29 (H-2'), 2.68 (H-2), 2.70 (H-10), 2.58 (H-3'), 2.46 (H-9a), 2.35 (H-4), 2.29 /3'N(CH$_3$)$_2$/, 2.30 (9a-NCH$_3$), 2.11 (H-9b), 1.94 (H-14a), 1.89 (H-8), 1.70 (H-4'a), 1.66 (H-7a), 1.54 (H-7b), 1.52 (H-14b), 1.33 (6-CH$_3$), 1.30 (2-CH$_3$), 1.27 (H-4'b), 1.25 (5'-CH$_3$), 1.12 (12-CH$_3$), 1.10 (4-CH$_3$), 1.06 (10-CH$_3$), 0.92 (8-CH$_3$), 0.86 (14-CH$_3$).

¹³C NMR (75 MHz, CDCl$_3$) δ175.7 (C-1), 106.1 (C-1'), 94.7 (C-5), 74.2 (C-12), 78.1 (C-3), 86.0 (C-11), 77.1 (C-13), 72.8 (C-6), 70.2 (C-2'), 70.9 (C-9), 65.4 (C-3'), 62.9 (C-10), 62.0 (11-OCH$_3$), 44.1 (C-2), 42.5 (C-7), 35.3 (C-4), 39.9 /3'N(CH$_3$)$_2$/, 36.2 (9a-NCH$_3$), 28.0 (C-4'), 26.7 (C-8), 25.8 (6-CH$_3$), 20.9 (8-CH$_3$), 21.2 (C-14), 20.8 (5'-CH$_3$), 16.8 (12-CH$_3$), 15.6 (2-CH$_3$), 10.3 (14-CH$_3$), 7.7 (4-HC$_3$), 6.8 (10-CH$_3$).

EXAMPLE 11

3-De(2,6-dideoxy-3-C-methyl-3-O-methyl-α-L-ribohexopyranosyl-oxy)-3-oxy-11-O-methyl-azithromycin 2'-O-acetate To a solution of 3-de(2,6-dideoxy-3-C-methyl-3-O-methyl-α-L-ribohexopyranosyl-oxy)-3-oxy-11-O-methyl-azithromycin (0.89 g) from Example 10 in CH$_2$Cl$_2$ (25 ml), NaHCO$_3$ (0.52 g) and acetic acid anhydride (0.15 ml) were added, the reaction mixture was stirred for 10 hours at room temperature, left standing over night and then isolated by means of extraction with CH$_2$Cl$_2$ as described in Example 5, yielding 0.65 g of a white amorphous precipitate.

| TLC, | Methylene chloride-methanol-conc. ammonia, 90:9:0.5 | Rf 0.426 |
|---|---|---|
| | Ethyl acetate-N-hexane-diethyl amine, 100:100:20 | Rf 0.670 |

IR (KBr) cm$^{-1}$ 3525, 3475, 2968, 2937, 1724, 1647, 1458, 1376, 1265, 1168, 1113, 1081, 1050.

EXAMPLE 12

3-De(2,6-dideoxy-3-C-methyl-3-O-methyl-α-L-ribohexopyranosyl-oxy)-11-O-methyl-azithromycin 3,6-hemiketal 2'-O-acetate To a solution of 3-de(2,6-dideoxy-3-C-methyl-3-O-methyl-α-L-ribohexopyranosyl-oxy)-3-oxy-11-O-methyl-azithromycin 2'-O-acetate (0.65 g) from Example 11 in CH$_2$Cl$_2$ (20 ml), dimethyl sulfoxide (0.94 ml) and N,N-dimethyl-aminopropyl-ethyl-carbodiimide (1.16 g) were added. The reaction mixture was cooled to 15° C. and then, under stirring and maintaining the temperature at 15° C., a solution of pyridinium trifluoroacetate (1.15 g) in CH$_2$Cl$_2$ (5 ml) was gradually added dropwise over 30 minutes. The temperature of the reaction mixture was raised to room temperature, it was stirred for further 4 hours and then a product was isolated according to the process described in Example 6, yielding 0.6 g of the title product.

| TLC, | Methylene chloride-methanol-conc. ammonia, 90:9:0.5 | Rf 0.606 |
|---|---|---|
| | Ethyl acetate-N-hexane-diethyl amine, 100:100:20 | Rf 0.861 |

EXAMPLE 13

3-De(2,6-dideoxy-3-C-methyl-3-O-methyl-α-L-ribohexopyranosyl-oxy)-11-O-methyl-azithromycin 3,6-hemiketal A solution of 3-de(2,6-dideoxy-3-C-methyl-3-O-methyl-α-L-ribohexopyranosyl-oxy)-11-O-methyl-azithromycin 3,6-hemiketal 2'-O-acetate (0.6 g) from Example 12 in methanol (40 ml) was left standing for 24 hours at room temperature. Methanol was evaporated at a reduced pressure, the obtained residue (0.53 g) was purified by low-pressure chromatography on a silica gel column using the system methylene chloride-methanol-conc. ammonia, 90:9:1.5. By evaporation of the combined extracts with Rf 0.670 there were obtained 0.22 g of chromatographically homogeneous 3-de(2,6-dideoxy-3-C-methyl-3-O-methyl-α-L-ribohexopyranosyl-oxy)-11-O-methyl-azitromycin 3,6-heminketal with the following physical-chemical constants:

IR (CDCl$_3$) cm$^{-1}$: 3471, 2975, 1715, 1638, 1458, 1382, 1196, 1117, 1049, 1013, 963.

¹H NMR (300 MHz, CDCl$_3$) δ: 5.01 (H-13), 4.22 (H-1'), 3.80 (H-5), 3.50 (H-5'), 3.45 (11-OCH$_3$), 3.25 (H-2'), 2.63 (H-2), 2.49 (H-3'), 2.77 (H-9a), 2.29 /3'N(CH$_3$)$_2$/, 2.20 (9a-NCH$_3$), 2.24 (H-9b), 2.09 (H-4), 1.85 (H-8), 1.83 (H-14a), 1.66 (H-4'a), 1.73 (H-14b), 1.36 (6-CH$_3$), 1.31 (2-CH$_3$), 1.26 (H-4'b), 1.21 (5'-CH$_3$), 1.25 (4-CH$_3$), 1.01 (10-CH$_3$), 1.03 (8-CH$_3$), 0.81 (14-CH$_3$).

¹³C NMR (75 MHz, CDCl$_3$) δ: 177.0 (C-1), 106.2 (C-1'), 102.1 (C-3), 93.9 (C-5), 86.1 (C-11), 81.9 (C-6), 69.7 (C-2'), 64.9 (C-9), 65.8 (C-3'), 62.1 (C-10), 61.9 (11-OCH$_3$), 49.6 (C-2), 43.3 (C-7), 40.1 /3'N(CH$_3$)$_2$/, 28.1 (C-4'), 28.7 (C-8), 25.5 (6-CH$_3$), 20.9 (5'-CH$_3$), 14.0 (2-CH$_3$), 11.7 (14-CH$_3$), 12.3 (4-CH$_3$), 8.5 (10-CH$_3$).

EXAMPLE 14

3-De(2,6-dideoxy-3-C-methyl-3-O-methyl-α-L-ribohexopyranosyl-oxy)-3-oxy-azithromycin 3-De(2,6-dideoxy-3-C-methyl-3-O-methyl-α-L-ribohexopyranosyl-oxy)-3-oxy-azithromycin was prepared from azithromycin according to the process by Djokićet al. from U.S. Pat. No. 4,886,792 of December 1989, Example 3. By separation on a silica gel column using the solvent system methylene chloride-methanol-conc. ammonia, 90:9:0.5, there was obtained a chromatographically homogeneous product with the following physical-chemical constants:

TLC, Ethyl acetate-triethyl amine, 95:5 Rf 0.371

IR (KBr) cm$^{-1}$: 3438, 2973, 2938, 1713, 1655, 1459, 1378, 1350, 1260, 1172, 1113, 1078, 1044, 957.

¹H NMR (300 MHz, CDCl$_3$) δ: 4.72 (H-13), 4.47 (H-1'), 3.78 (H-3), 3.58 (H-5), 3.56 (H-5'), 3.65 (H-11), 3.27 (H-2'), 2.66 (H-2), 2.74 (H-10), 2.52 (H-3'), 2.49 (H-9a), 2.28 (H-4), 2.26 /3'N(CH$_3$)$_2$/, 2.37 (9a-NCH$_3$), 2.06 (H-9b), 1.90 (H-14a), 1.90 (H-8), 1.67 (H-4'a), 1.62 (H-7a), 1.47 (H-7b), 1.53 (H-14b), 1.32 (6-CH$_3$), 1.30 (2-CH$_3$), 1.28 (H-4'b), 1.26 (5'-CH$_3$), 1.07 (12-CH$_3$), 1.06 (4-CH$_3$), 1.12 (10-CH$_3$), 0.92 (8-CH$_3$), 0.88 (14-CH$_3$).

¹³C NMR (75 MHz, CDCl$_3$) δ: 178.8 (C-1), 106.6 (C-1'), 94.7 (C-5), 72.9 (C-12), 79,2 (C-3), 75.5 (C-11), 77.1 (C-13), 74.0 (C-6), 70.3 (C-2'), 70.6 (C-9), 65.4 (C-3'), 62.2 (C-10), 44.2 (C-2), 41.7 (C-7), 35.6 (C-4), 39.9 /3'N(CH$_3$)$_2$/, 36.8 (9a-NCH$_3$), 27.7 (C-4'), 26.3 (C-8), 25.5 (6-CH$_3$), 20.8 (8-CH$_3$), 20.5 (C-14), 20.9 (5'-CH$_3$), 15.7 (12-CH$_3$), 15.8 (2-CH$_3$), 10.5 (14-CH$_3$), 7.5 (4-CH$_3$), 7.3 (10 -CH$_3$).

EXAMPLE 15

3-De(2,6-dideoxy-3-C-methyl-3-O-methyl-α-L-ribohexopyranosyl-oxy)-3-oxy-azithromycin 2'-O-acetate To a solution of 3-de(2,6-dideoxy-3-C-methyl-3-O-methyl-α-L-ribohexopyranosyl-oxy)-3-oxy-azithromycin (10 g) from Example 14 in CH$_2$Cl$_2$ (150 ml), NaHCO$_3$ (5.84 g) and acetic acid anhydride (1.68 ml) were added. The reaction mixture was stirred for 12 hours at room temperature, left standing over night and then isolated according to the process described in Example 5, yielding 11.21 g of an amorphous precipitate with the following physical-chemical constants:

TLC Ethyl acetate-triethyl amine, 95:5 Rf 0.547

IR (KBr) cm$^{-1}$: 3485, 2973, 2937, 1748, 1716, 1648, 1459, 1376, 1240, 1170, 1114, 1081, 1045, 956.

$^1$H NMR (300 MHz, CDCl$_3$) δ: 4.71 (H-13), 4.79 (H-2'), 4.71 (H-1'), 3.84 (H-3), 3.61 (H-5), 3.50 (H-5'), 3.68 (H-11), 2.73 (H-10), 2.70 (H-2), 2.70 (H-3'), 2.48 (H-9a), 2.27 (H-4), 2.26 /3'N(CH$_3$)$_2$/ , 2.36 (9a-NCH$_3$), 2.07 (COCH$_3$), 2.05 (H-9b), 1.90 (H-14a), 1.90 (H-8), 1.78 (H-4'a), 1.56 (H-7a), 1.24 (H-7b), 1.54 (H-14b), 1.23 (6-CH$_3$), 1.29 (2-CH$_3$), 1.32 (H-4'b), 1.24 (5'-CH$_3$), 1.11 (10-CH$_3$), 1.06 (12-CH$_3$), 0.90 (4-CH$_3$), 0.89 (8-CH$_3$), 0.88 (14-CH$_3$).

EXAMPLE 16

3-De(2,6-dideoxy-3-C-methyl-3-O-methyl-α-L-ribohexopyranosyl-oxy)-azithromycin-3,6-hemiketal 2'-O-acetate To a solution of 3-de(2,6-dideoxy-3-C-methyl-3-O-methyl-α-L-ribo-hexopyranosyl-oxy)-3-oxy-azithromycin 2'-O-acetate (5.6 g) from Example 15 in CH$_2$Cl$_2$ (100 ml), dimethyl sulfoxide (12.34 ml) and N,N-dimethyl-aminopropyl-ethyl-carbodiimide (15.05 g) were added. The reaction mixture was cooled to 15° C. and then, under stirring and maintaining the temperature at 15° C., a solution of pyridinium trifluoracetate (15.04 g) in CH$_2$Cl$_2$ (30 ml) was added gradually drop by drop over 30 minutes. The temperature of the reaction mixtue was raised to room temperature, it was kept stirring for further 4 hours and then a product was isolated in accordance with the process described in Example 6, yielding 5.26 g of the title product.

TLC Ethylacetate-trietyl amine, 95:5 Rf 0.675

EXAMPLE 17

3-De(2,6-dideoxy-3-C-methyl-3-O-methyl-α-L-ribohexopyranosyl-oxy)-azithromycin 3,6-hemiketal A solution of 3-de(2,6-dideoxy-3-C-methyl-3-O-methyl-α-L-ribohexopyranosyl-oxy)-azithromycin-3,6-hemiketal 2'-O-acetate (5.2 g) from Example 16 in methanol (100 ml) was left standing for 16 hours at room temperature. Methanol was evaporated at a reduced pressure and the obtained product was purified by low-pressure chromatography on a silica gel column using the system methylene chloride-methanol-conc. ammonia, 90:9:1.5. By evaporating the combined fractions with Rf 0.480 there was obtained chromatographically homogeneous 3-de(2,6-dideoxy-3-C-methyl-3-O-methyl-α-L-ribohexopyranosyl-oxy)-azithromycin 3,6-hemiketal with the following physical-chemical constants:

TLC Ethyl acetate-triethyl amine, 95:5 Rf 0.447

IR(CDCl$_3$) cm$^{-1}$: 3468, 2976, 1713, 1638, 1459, 1382, 1197, 1116, 1068, 1049, 1014, 963.

$^1$H NMR (300 MHz,CDCl$_3$) δ: 4.94 (H-13), 4.21 (H-1'), 3.74 (H-5), 3.51 (H-5'), 3.23 (H-2'), 2.57 (H-2), 2.49 (H-3'), 2.23 /3'N(CH$_3$)$_2$/, 2.06 (H-4), 1.74 (H-8), 1.67 (H-4'a), 1.39 (6-CH$_3$), 1.28 (2-CH$_3$), 1.25 (H-4'b), 1.22 (5'-CH$_3$), 1.23, (4-CH$_3$), 1.10 (10-CH$_3$), 1.04 (8-CH$_3$), 0.92 (14-CH$_3$).

$^{13}$C NMR (75 MHz, CDCl$_3$) δ: 176.9 (C-1), 106.1 (C-1'), 102.3 (C-3), 94.8 (C-5), 82.4 (C-6), 69.7 (C-2'), 68.5 (C-11), 66.4 (C-9), 65.3 (C-3'), 61.6 (C-10), 49.3 (C-2), 41.6 (C-7), 40.1 /3'N(CH$_3$)$_2$/, 31.0 (C-8), 28.2 (C-4'), 26.4 (6-CH$_3$), 20.8 (5'-CH$_3$), 13.6 (2-CH$_3$), 12.6 (4-CH$_3$), 11.4 (14-CH$_3$).

FAB-MS m/z 589

EXAMPLE 18

3-De(2,6-dideoxy-3-C-methyl-3-O-methyl-α-L-ribohexopyranosyl-oxy)-azithromycin 3,6-hemiketal 11,12-cyclic carbonate To a solution of 3-de(2,6-dideoxy-3-C-methyl-3-O-methyl-α-L-ribohexopyranosyl-oxy)-azithromycin 3,6-hemiketal (1 g) from Example 17 in ethyl acetate (30 ml), ethylene carbonate (0.5 g) and potassium carbonate (0.5 g) were added. The reaction suspension was stirred under reflux for 10 hours, left standing for 16 hours at room temperature and then filtered. Ethyl acetate was rinsed with saturated NaCl solution and water, dried over CaCl$_2$, filtered and evaporated, yielding 1.05 g of an oily residue. After separation on a silica gel column using the system methylene chloride-methanol-conc. ammonia, 90:9:0.5, there was obtained chromatographically homogenous title product with the following physical-chemical constants:

TLC Ethyl acetate-tniethyl amine, 95:5 Rf 0.514

IR(CDCl$_3$) cm$^{-1}$: 3498, 2975, 2941, 1812, 1724, 1638, 1459, 1381, 1359, 1333, 1292, 1234, 1173, 1115, 1082, 1045, 1015, 966.

$^1$H NMR (300 MHz, CDCl$_3$) δ: 5.03 (H-13), 4.61 (H-11), 4.23 (H-1'), 3.73 (H-5), 3.52 (H-5'), 3.25 (H-2'), 3.18 (H-9a), 2.90 (H-10), 2.54 (H-2), 2.50 (H-3'), 2.28 /3'N(CH$_3$)$_2$/, 2.10 (H-4), 2.07 (9a-NCH$_3$), 1.76 (H-7a), 1.95 (H-8), 1.86 (H-14a), 1.67 (H-4'a), 1.57 (H-9b), 1.55 (H-14b), 1.45 (12-CH$_3$), 1.37 (6-CH$_3$), 1.30 (2-CH$_3$), 1.28 (H-4'b), 1.23 (5'-CH$_3$), 1.24 (4-CH$_3$), 1.13 (H-7b), 1.18 (10-CH$_3$), 0.90 (8-CH$_3$), 0.92 (14-CH$_3$).

$^{13}$C NMR (75 MHz, CDCl$_3$) δ: 176.1 (C-1), 153.5 C=O carbonate), 106.1 (C-1'), 101.6 (C-3), 93.6 (C-5), 83.7 (C-12), 82.7 (C-6), 78.9 (C-11), 77.9 (C-13), 69.6 (C-2'), 69.4 (C-5'), 63.6 (C-9), 65.3 (C-3'), 60.1 (C-10), 49.9 (C-2), 46.6 (C-4), 41.8 (C-7), 40.0/3'N(CH$_3$)$_2$/, 33.4 (9a-CH$_3$), 28.0 (C-4'), 26.8 (C-8), 25.1 (6-CH$_3$), 22.3 (C-14), 20.8 (5'-CH$_3$), 19.4 (8-CH$_3$), 14.1 (12-CH$_3$), 13.9 (2-CH$_3$), 12.1 (4-CH$_3$), 12.9 (10-CH$_3$), 10.1 (14-CH$_3$).

What is claimed is:

1. A compound of the formula (I)

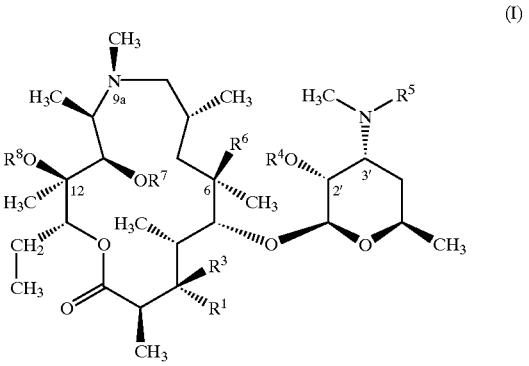

characterized in that

R$^1$ individually stands for hydroxyl or a L-cladinosyl group of the formula (II)

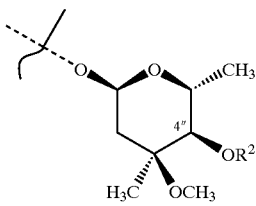

(II)

wherein
- $R^2$ individually stands for a silyl group,
- $R^3$ individually stands for hydrogen or together with $R^6$ stands for an ether group,
- $R^4$ individually stands for hydrogen, $(C_1-C_4)$acyl group or —COO—$(CH_2)_n$—Ar group, wherein n is 1–7 and Ar individually stands for an unsubstituted or substituted aryl group with up to 18 carbon atoms,
- $R^5$ individually stands for hydrogen, methyl group or —COO—$(CH_2)_n$—Ar group, wherein n is 1–7 and Ar individually stands for an unsubstituted or substituted aryl group with up to 18 carbon atoms,
- $R^6$ individually stands for hydroxyl group or together with $R^3$ stand for an ether group,
- $R^7$ individually stands for hydrogen, $(C_1-C_{12})$alkyl group, silyl group or together with $R^8$ and C-11/C-12 carbon atoms stands for a cyclic carbonate,
- $R^8$ individually stands for hydrogen, $(C_1-C_{12})$alkyl group, silyl group or together with $R^7$ and C-11/C-12 carbon atoms for a cyclic carbonate, or a pharmaceutically acceptable addition salts with an inorganic or organic acid.

2. Compound according to claim 1, characterized in that $R^1$ stands for L-cladinosyl group, $R^2$ and $R^7$ are mutually the same and stand for trimethylsilyl group, $R^3$ and $R^8$ are mutually the same and stand for hydrogen, $R^4$ and $R^5$ are mutually the same and stand for benzyloxycarbonyl group and $R^6$ is hydroxyl group.

3. Compound according to claim 1, characterized in that $R^1$ stands for L-cladinosyl group, $R^2$ stands for trimethylsilyl group, $R^3$, $R^7$ and $R^8$ are mutually the same and stand for hydrogen, $R^4$ and $R^5$ are mutually the same and stand for benzyloxy-carbonyl group and $R_6$ is hydroxyl group.

4. Compound according to claim 1, characterized in that $R^1$ stands for L-cladinosyl group, $R^2$ and $R^7$ are mutually the same and stand for trimethylsilyl group, $R^3$ stands for hydrogen, $R^4$ and $R^5$ are mutually the same and stand for benzyloxy-carbonyl group, $R^6$ is hydroxyl group and $R^8$ is methyl.

5. Compound according to claim 1, characterized in that $R^1$ stands for L-cladinosyl group, $R^2$ stands for trimethylsilyl group, $R^3$ and $R^8$ are mutually the same and stand for hydrogen, $R^4$ and $R^5$ are mutually the same and stand for benzyloxy-carbonyl group, $R^6$ stands for hydroxyl group and $R^7$ is methyl.

6. Compound according to claim 1, characterized in that $R^1$ stands for L-cladinosyl group, $R^2$ stands for trimethylsilyl group, $R^3$ and $R^7$ are mutually the same and stand for hydrogen, $R^4$ and $R^5$ are mutually the same and stand for benzyloxy-carbonyl group, $R^6$ is hydroxyl group and $R^8$ is methyl.

7. Compound according to claim 1, characterized in that $R^1$ and $R^6$ are mutually the same and stand for hydroxyl group, $R^3$, $R^4$ and $R^8$ are mutually the same and stand for hydrogen and $R^5$ and $R^7$ are mutually the same and stand for methyl.

8. Compound according to claim 1, characterized in that $R^1$ and $R^6$ are mutually the same and stand for hydroxyl group, $R^3$, $R^4$ and $R^7$ are mutually the same and stand for hydrogen and $R^5$ and $R^8$ are mutually the same and stand for methyl.

9. Compound according to claim 1, characterized in that $R^1$ and $R^6$ are mutually the same and stand for hydroxyl group, $R^3$, $R^7$ and $R^8$ are mutually the same and stand for hydrogen, $R^4$ is acetyl and $R^5$ is methyl.

10. Compound according to claim 1, characterized in that, $R^1$ and $R^6$ are mutually the same and stand for hydroxyl group, $R^3$ and $R^8$ are mutually the same and stand for hydrogen, $R^4$ is acetyl and $R^5$ and $R^7$ are mutually the same and stand for methyl.

11. Compound according to claim 1, characterized in that $R^1$ and $R^6$ are mutually the same and stand for hydroxyl group, $R^3$ and $R^7$ are mutually the same and stand for hydrogen, $R^4$ is acetyl and $R^5$ and $R^8$ are mutually the same and stand for methyl.

12. Compound according to claim 1, characterized in that $R^1$ stands for hydroxyl group, $R^3$ together with $R^6$ stands for an ether group, $R^4$ is acetyl, $R^5$ is methyl, $R^7$ and $R^8$ are mutually the same and stand for hydrogen.

13. Compound according to claim 1, characterized in that $R^1$ stands for hydroxyl group, $R^3$ together with $R^6$ stands for an ether group, $R^4$ is acetyl, $R^5$ and $R^7$ are mutually the same and stand for methyl, and $R^8$ is hydrogen.

14. Compound according to claim 1, characterized in that $R^1$ stands for hydroxyl group, $R^3$ together with $R^6$ stands for an ether group, $R^4$ is acetyl, $R^5$ and $R^8$ are mutually the same and stand for methyl and $R^7$ is hydrogen.

15. Compound according to claim 1, characterized in that $R^1$ stands for hydroxyl group, $R^3$ together with $R^6$ stands for an ether group, $R^4$, $R^7$ and $R^8$ are mutually the same and stand for hydrogen, and $R^5$ is methyl.

16. Compound according to claim 1, characterized in that $R^1$ stands for hydroxyl group, $R^3$ together with $R^6$ stands for an ether group, $R^4$ and $R^8$ are mutually the same and stand for hydrogen and $R^5$ and $R^7$ are mutually the same and stand for methyl.

17. Compound according to claim 1, characterized in that $R^1$ stands for hydroxyl group, $R^3$ together with $R^6$ stands for an ether group, $R^4$ and $R^7$ are mutually the same and stand for hydrogen and $R^5$ and $R^8$ are mutually the same and stand for methyl.

18. Compound according to claim 1, characterized in that $R^1$ stands for hydroxyl group, $R^3$ together with $R^6$ stands for an ether group, $R^4$ is hydrogen, $R^5$ is methyl and $R^7$ and $R^8$ together with C-11/C-12 carbon atoms stand for a cyclic carbonate.

19. A process for the preparation of compounds of the formula (I)

(I)

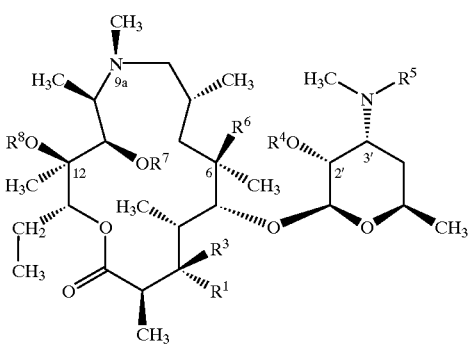

wherein

R$^1$ individually stands for hydroxyl or a L-cladinosyl group of the formula (II)

(II)

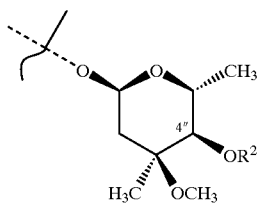

wherein

R$^2$ individually stands for a silyl group,

R$^3$ individually stands for hydrogen or together with R$^6$ stands for an ether group, R$^4$ individually stands for hydrogen, (C$_1$–C$_4$)acyl group or —COO—(CH$_2$)$_n$—Ar group, wherein n is 1–7 and Ar individually stands for unsubstituted or substituted aryl group with up to 18 carbon atoms, R$^5$ individually stands for hydrogen, methyl group or —COO—(CH$_2$)$_n$—Ar group, wherein n is 1–7 and Ar individually stands for unsubstituted or substituted aryl group with up to 18 carbon atoms.

R$^6$ individually stands for hydroxyl group or together with R$^3$ stands for an ether group, R$^7$ individually stands for hydrogen, (C$_1$–C$_{12}$)alkyl group, silyl group or together with R$^8$ and C-11/C-12 carbon atoms stands for acyclic carbonate, R$^8$ individually stands for hydrogen, (C$_1$–C$_{12}$)alkyl group, silyl group or together with R$^7$ and C-11/C-12 carbon atoms stands for a cyclic carbonate, or a pharmaceutically acceptable addition salt with an inorganic or organic acid, characterized in that (I) azithromyein of the formula (I), wherein R$^1$ stands for L-cladinosyl group of the formula (II), R$^2$ stands for a silyl group, and wherein, R$^3$, R$^4$, R$^7$ and R$^8$ are mutually the same and stand for hydrogen, R$^5$ is methyl and R$^6$ is hydroxyl group, is subjected to a reaction with organic carboxylic acid chlorides of the formula (III)

 (III)

wherein n is 1–7 and Ar individually stands for unsubstituted or substituted aryl group with up to 18 carbon atoms in the presence of a first bases in a first reaction-inert solvent, yielding a compound of the general formula (I), wherein R$^1$ stands for L-cladinosyl group of formula (II), R$^2$ stands for a silyl group, and wherein, R$^3$, R$^7$ and R$^8$ are mutually the same and stand for hydrogen, R$^4$ and R$^5$ are mutually the same and stand for benzyloxycarbonyl group and R$^6$ is hydroxyl group, which is subsequently subjected to a selective silylation of hydroxyl groups in A/4 4"- and 11-positions with 2–5 equimolar excess of a silylating agent in an organic inert solvent at a temperature 0–5° C. during 5–8 hours, yielding a compound of the formula (I), wherein R$^1$ stands for trimethylsilyl group, R$^3$ and R$^8$ are mutually the same and stand for hydrogen, R$^4$ and R$^5$ are mutually the same and stand for benzyloxycarbonyl group and R$^6$ is hydroxyl group, or in B/ 4"-position with 1.1–2 equimolar excess of a silylating agent, in an organic inert solvent at a temperature 0.5° C., during a 1 hour, yielding a compound of formula (I), wherein R$^1$ stands for L-cladinosyl group of the formula (II), R$^2$ stands for trimethylsilyl group, R$^3$, R$^7$ and R$^8$ are mutually the same and stand for hydrogen, R$^4$ and R$^5$ are mutually the same and stand for benzyloxycarbonyl group and R$^6$ stands for hydroxyl group, which are then subjected to O-alkylation with 1.3 to 10 molar excess of corresponding alkylating agent in the presence of 1.1–8.5 moles of a second base in a second reaction-inert solvent at an O-alkylation temperature from −15° C. to room temperature yielding in the case of A/ a compound of formula (I), wherein R$^1$ stands for L-cladinosyl group of the formula III), R$^2$ and R$^7$ are mutually the same and stand for trimethylsilyl group, R$^3$ stands for hydrogen, R$^4$ and R$^5$ are mutually the same and stand for benzyloxycarbonyl group, R$^6$ is hydroxyl group and R$^8$ is methyl, or in the case of B/ a mixture of a compound of the formula (I), wherein R$^1$ stands for L-cladinosyl group of the formula (II), R$^2$ stands for trimethylsilyl group, R$^3$ and R$^8$ are mutually the same and stand for hydrogen, R$^4$ and R$^5$ are mutually the same and stand for benzyloxycarbonyl group, R$^6$ stands for hydroxyl group and R$^7$ is methyl, and of a compound of the general formula (I), wherein R$^1$ stands for L-cladinosyl group of the formula (II), R$^3$ ad R$^7$ are mutually the same and stand for hydrogen, R$^4$ and R$^5$ are mutually the same and stand for benzyloxycarbonyl group, R$^6$ is hydroxyl group and R$^8$ is methyl, which are then subjected to deprotection of the protecting groups in 2'- and 3'-positions in a solution of a first lower alcohol in the presence of NaOAc/HOAc buffer (pH 5) and of a catalyst in hydrogen atmosphere at a pressure of 1–20 bars and then after isolation, to desilylation in 4"- and 11-positions in a second lower alcohol in the presence of formic acid, yielding in the case of A/ a compound of the general formula (I), wherein R$^1$ stands for L-cladinosyl group of the formula (II), R$^1$, R$^2$ stands for a silyl group, and wherein, R$^3$, R$^4$, R$^5$ and R$^7$ are mutually the same and stand for hydrogen, R$^6$ is hydroxyl group and R$^8$ is methyl, or in the case of B/ a mixture of a compound of the general formula (I), wherein R$^1$ stands for L-cladinosyl group of the formula (II), R$^2$, R$^3$, R$^4$, R$^5$ and R$^8$ are mutually the same and stand for hydrogen, R$^6$is hydroxyl group and R$^7$ is methyl, and of a compound of formula (I), wherein R$^1$, R$^2$ stands for a silyl group, and wherein, R$^3$, R$^4$, R$^5$, R$^7$ and R$^8$ have the meanings as given for deprotection in the case of A/, which are then subjected to reductive 3'-N-methylation with 1–3 equivalents of formaldehyde (37%) in the presence of an equal or double quantity of formic acid (98–100%) and hydrogenation catalyst or of some other hydrogen source, in a third reaction-inert solvent at an elevated temperature, yielding in the case of A/ a compound of the general formula (I), wherein $R^1$ stands for L-cladinosyl group of the formula (II), $R^2$ stands for a silyl group, and wherein, $R^3$, $R^4$ and $R^7$ are mutually the same and stand for hydrogen, $R^5$ and $R^8$ are mutually the same and stand for methyl and $R^6$ is hydroxyl group, or in the case of B/ a mixture of a compound of the general formula (I), wherein $R^1$ stands for L-cladinosyl group of the formula (II), $R^2$ stands for a silyl group, and wherein, $R^3$, $R^4$, $R^5$ and $R^8$ are mutually the same and stand for hydrogen $R^5$ and $R^7$ are mutually the same and stand for methyl and $R^6$ is hydroxyl group and $R^7$ is methyl, and of a compound of formula (I), wherein $R^1$, $R^2$, $R^3$, $R^4$, $R^5$, $R^7$ and $R^8$ have the meanings as given for deprotection in the case of A/, which is then optionally subjected to separation on a silica gel column, yielding a chromatographically homogeneous compound of formula (I), wherein $R^1$ stands for L-cladinosyl group, $R^2$, $R^3$, $R^4$, and $R^8$ are mutually the same and stand for hydrogen, $R^5$ and $R^7$ are mutually the same and stand for methyl and $R^6$ stands for hydroxyl group (11-O-methyl-azithromycin) and a compound of formula (I), wherein $R^1$, $R^2$, $R^3$, $R^4$, $R^5$ $R^6$, $R^7$ and $R^8$ have the meanings as given for 3'-N-methylation in the case of A/ (12-O-methyl azithromycin), or that (II) acithromycin or its 11-O-methyl- and 12-O-methyl-derivatives obtained according to the process (I) are optionally subjected to a reaction of hydrolysis with diluted inorganic acids yielding a compound of formula (I), wherein $R^1$ and $R^6$ are mutually the same and stand for hydroxyl group, $R^3$, $R^4$ and $R^8$ are mutually the same and stand for hydrogen, and $R^5$ and $R^7$ are mutually the same and stand for methyl, or a compound of formula (I), wherein $R^1$ and $R^6$ are mutually the same and stand for hydroxyl group, $R^3$, $R^4$ and $R^7$ are mutually the same and stand for hydrogen, and $R^5$ and $R^8$ are mutually the same and stand for methyl, which are then optionally subjected to a reaction of selective acylation of hydroxyl group in 2'-position with chlorides and anhydrides of carboxylic acids with up to 4 carbon atoms in a fourth reaction-inert organic solvent yielding a compound of formula (I), wherein $R^1$ and $R^6$ are mutually the same and stand for hydroxyl group, $R^3$, $R^7$ and $R^8$ are mutually the same and stand for hydrogen, $R^4$ is acetyl and $R^5$ is methyl, or a compound of formula (I), wherein $R^1$ and $R^6$ are mutually the same and stand for hydroxyl group, $R^3$ and $R^8$ are mutually the same and stand for hydrogen, $R^4$ is acetyl and $R^5$ and $R^7$ are mutually the same and stand for is methyl, or a compound of formula (I), wherein $R^1$ and $R^6$ are mutually the same and stand for hydroxyl group, $R^3$ and $R^7$ are mutually the same and stand for hydrogen, $R^4$ is acetyl and $R^5$ and $R^8$ are mutually the same and stand for methyl, which are then optionally subjected to oxidation with Jones reagent or according to a modified Moffat-Pfitzner process in the presence of dimethyl sulfoxide and pyridinium trifluoracetate as a catalyst, in a fourth reaction-inert organic solvent at a temperature from 10° C. to room temperature, yielding a compound of formula (I), wherein $R^1$ stands for hydroxyl group, $R^3$ together with $R^6$ stands for an ether group, $R^4$ is acetyl, $R^5$ is methyl, $R^7$ and $R^8$ are mutually the same and stand for hydrogen, or a compound of formula (I), wherein $R^1$ stands for a hydroxyl group, $R^3$ together with $R^6$ stands for an ether group, $R^4$ is acetyl, $R^5$ and $R^7$ are mutually the same and stand for methyl and $R^8$ is hydrogen, or a compound of the general formula (I), wherein $R^1$ stands for a hydroxyl group, $R^3$ together with $R^6$ stands for an ether group, $R^4$ is acetyl, $R^5$ and $R^8$ are mutually the same and stand for methyl and $R^7$ is hydrogen, which are then subjected to a deacylation reaction in 2'-position by means of solvolysis in a third lower alcohol at room temperature, yielding a compound of formula (I), wherein $R^1$ stands for hydroxyl group, $R^3$ together with $R^6$ stands for an ether group, $R^4$, $R^7$ and $R^8$ are mutually the same and stand for hydrogen, and $R^5$ is methyl, or a compound of formula (I), wherein $R^1$ stands for hydroxyl group, $R^3$ together with $R^6$ stands for an ether group, $R^4$ and $R^8$ are mutually the same and stand for hydrogen, and $R^5$ and $R^7$ are mutually the same and stand for hydroxyl group, $R^3$ together with $R^6$ stands for an ether group, $R^4$ and $R^7$ are mutually the same and stand for hydrogen, and $R^5$ and $R^8$ are mutually the same and stand for methyl, and then a compound of formula (I), wherein $R^1$ stands for hydroxyl group, $R^3$ together with $R^6$ stands for an ether group, $R^4$, $R^7$ and $R^8$ are mutually the same and stand for hydrogen and $R^5$ is methyl, are optionally subjected to a reaction with ethylene carbonate in the presence of an inorganic or organic in a fifth reaction-inert solvent yielding a compound of formula (I), wherein $R^1$ stands for hydroxyl group, $R^3$ together with $R^6$ stands for an ether group, $R^4$ is hydrogen, $R^5$ is methyl, and $R^7$ and $R^8$ together with C-11/C-12 carbon atoms stand for a cyclic carbonate.

20. Pharmaceutical composition useful in the treatment of bacterial infections in humans or animals comprising antibacterially effective amounts of a compound of formula (I) or its pharmaceutically acceptable addition salts according to claim 1 in a combination with a pharmaceutically acceptable carrier.

21. A method of treatment of bacterial infections in humans or animals comprising the administration of an antibacterially effective amount of a compound of formula (I) or its pharmaceutically acceptable salts with inorganic or organic acids according to claim 1 in a combination with a pharmaceutically acceptable carrier to humans or animals in need of such treatment.

\* \* \* \* \*